US008721857B2

(12) United States Patent
Murai et al.

(10) Patent No.: US 8,721,857 B2
(45) Date of Patent: May 13, 2014

(54) GAS SENSOR ELEMENT AND ITS MANUFACTURING METHOD, AND GAS SENSOR EMPLOYING THE GAS SENSOR ELEMENT

(75) Inventors: Atsushi Murai, Kuwana (JP); Hiroyuki Yamamoto, Kariya (JP)

(73) Assignee: Denso Corporation, Kariya (JP)

( * ) Notice: Subject to any disclaimer, the term of this patent is extended or adjusted under 35 U.S.C. 154(b) by 186 days.

(21) Appl. No.: 13/480,934

(22) Filed: May 25, 2012

(65) Prior Publication Data

US 2012/0297861 A1 Nov. 29, 2012

(30) Foreign Application Priority Data

May 27, 2011 (JP) ................................. 2011-118948

(51) Int. Cl.
*G01N 27/407* (2006.01)

(52) U.S. Cl.
CPC ................................. *G01N 27/4077* (2013.01)
USPC ........... 204/429; 204/421; 204/424; 204/426; 204/428

(58) Field of Classification Search
CPC ....................... G01N 27/4077; G01N 27/4118
USPC .................... 204/421, 424, 426–429
See application file for complete search history.

(56) References Cited

U.S. PATENT DOCUMENTS 6,569,303 B1* 5/2003 Moriguchi et al. ............ 204/426
2009/0255812 A1* 10/2009 Yoshida et al. ................ 204/431

FOREIGN PATENT DOCUMENTS

| JP | 2003-322632 | 11/2003 |
|----|-------------|---------|
| JP | 2007-033374 | 2/2007 |
| JP | 2007-199046 | 8/2007 |
| JP | 2007-206055 | 8/2007 |
| JP | 2008-216241 | 9/2008 |
| JP | 2009-075012 | 4/2009 |
| JP | 2009-080110 | 4/2009 |
| JP | 2010-169655 | 8/2010 |
| JP | 2010-256111 | 11/2010 |
| JP | 2010-276530 | 12/2010 |
| JP | 2011-089796 | 5/2011 |
| JP | 2011-252894 | 12/2011 |

* cited by examiner

*Primary Examiner* — J. Christopher Ball
(74) *Attorney, Agent, or Firm* — Nixon & Vanderhye PC

(57) ABSTRACT

A gas sensor element includes a main body and a protective layer. The main body has four plane portions and four corner portions each of which is formed between one adjacent pair of the plane portions. The four corner portions include a pair of first corner portions that are formed on a porous diffusion-resistant layer side in a lamination direction of the main body and a pair of second corner portions that are formed on a heater layer side in the lamination direction. The protective layer is comprised of an inner protective layer that covers at least the first corner portions of the main body and an outer protective layer that covers the entire outer periphery of the main body and the inner protective layer. The protective layer has a larger average thickness at the first corner portions than at the plane portions of the main body.

16 Claims, 20 Drawing Sheets

FIG.10A

| SAMPLE | THICKNESS (μm) | WEIGHT (mg) | OCCURENCE OF CRACKS | ACTIVATION TIME |
|---|---|---|---|---|
| E1 | 44 | 2.6 | × | ○ |
| E2 | 48 | 3.1 | × | ○ |
| E3 | 57 | 6 | ○ | ○ |
| E4 | 76 | 6.5 | ○ | ○ |
| E5 | 75 | 9.5 | ○ | ○ |
| E6 | 83 | 15 | ○ | ○ |
| E7 | 99 | 7.8 | ○ | ○ |
| E8 | 121 | 13 | ○ | ○ |
| E9 | 156 | 24 | ○ | ○ |
| E10 | 169 | 16 | ○ | ○ |
| E11 | 189 | 12 | ○ | ○ |
| E12 | 208 | 32 | ○ | ○ |
| E13 | 218 | 16.2 | ○ | ○ |
| E14 | 263 | 28 | ○ | ○ |
| E15 | 298 | 35 | ○ | ○ |
| E16 | 335 | 23.1 | ○ | ○ |
| E17 | 368 | 42 | ○ | ○ |
| E18 | 398 | 41 | ○ | ○ |
| E19 | 405 | 32 | ○ | ○ |
| E20 | 412 | 48 | ○ | ○ |
| E21 | 442 | 31 | ○ | ○ |
| E22 | 466 | 36 | ○ | ○ |
| E23 | 486 | 52 | ○ | ○ |
| E24 | 505 | 46 | ○ | ○ |
| E25 | 545 | 46 | ○ | ○ |
| E26 | 548 | 36 | ○ | ○ |
| E27 | 553 | 43.4 | ○ | ○ |
| E28 | 580 | 53 | ○ | ○ |
| E29 | 624 | 42 | ○ | ○ |
| E30 | 627 | 54 | ○ | ○ |
| E31 | 657 | 63 | ○ | ○ |
| E32 | 657 | 46 | ○ | ○ |
| E33 | 702 | 64 | ○ | ○ |
| E34 | 723 | 68 | ○ | × |
| E35 | 751 | 52 | ○ | ○ |
| E36 | 756 | 74 | ○ | × |

FIG.10B

| SAMPLE | THICKNESS (μm) | WEIGHT (mg) | OCCURENCE OF CRACKS | ACTIVATION TIME |
|---|---|---|---|---|
| C1 | 20 | 8 | × | ○ |
| C2 | 29 | 11 | × | ○ |
| C3 | 35 | 18 | × | ○ |
| C4 | 50 | 20 | ○ | ○ |
| C5 | 59 | 26 | ○ | ○ |
| C6 | 120 | 25 | ○ | ○ |
| C7 | 125 | 33 | ○ | ○ |
| C8 | 140 | 51 | ○ | ○ |
| C9 | 140 | 38 | ○ | ○ |
| C10 | 151 | 62 | ○ | ○ |
| C11 | 183 | 75 | ○ | × |
| C12 | 190 | 32 | ○ | ○ |
| C13 | 205 | 43 | ○ | ○ |
| C14 | 205 | 80 | ○ | × |
| C15 | 218 | 60 | ○ | ○ |
| C16 | 220 | 52 | ○ | ○ |
| C17 | 220 | 68 | ○ | × |
| C18 | 256 | 55 | ○ | ○ |
| C19 | 260 | 76 | ○ | × |
| C20 | 310 | 65 | ○ | ○ |
| C21 | 330 | 78 | ○ | × |
| C22 | 151 | 62 | ○ | ○ |
| C23 | 183 | 75 | ○ | × |
| C24 | 190 | 32 | ○ | ○ |
| C25 | 205 | 43 | ○ | ○ |
| C26 | 205 | 80 | ○ | × |
| C27 | 218 | 60 | ○ | ○ |
| C28 | 220 | 52 | ○ | ○ |
| C29 | 220 | 68 | ○ | × |
| C30 | 256 | 55 | ○ | ○ |
| C31 | 260 | 76 | ○ | × |
| C32 | 310 | 65 | ○ | ○ |
| C33 | 330 | 78 | ○ | × |

GAS SENSOR ELEMENT AND ITS MANUFACTURING METHOD, AND GAS SENSOR EMPLOYING THE GAS SENSOR ELEMENT

CROSS-REFERENCE TO RELATED APPLICATION

This application is based on and claims priority from Japanese Patent Application No. 2011-118948, filed on May 27, 2011, the content of which is hereby incorporated by reference in its entirety into this application.

BACKGROUND

1. Technical Field

The present invention relates to a gas sensor element for sensing the concentration of a specific component in a gas to be measured (to be simply referred to as a measurement gas hereinafter), a method of manufacturing the gas sensor element, and a gas sensor that employs the gas sensor element.

2. Description of Related Art

In exhaust systems of internal combustion engines of motor vehicles, there are generally provided gas sensors for sensing the concentration of a specific component (e.g., oxygen) in the exhaust gas (i.e., the measurement gas) from the engine.

Moreover, the gas sensors generally have a gas sensor element embedded therein. The gas sensor element has a main body that includes: a solid electrolyte body having oxygen ion conductivity and an opposite pair of first and second surfaces; a measurement electrode provided on the first surface of the solid electrolyte body so as to be exposed to the measurement gas; a reference electrode provided on the second surface of the solid electrolyte body so as to be exposed to a reference gas (e.g., air); and a porous diffusion-resistant layer through which the measurement gas is introduced to the measurement electrode.

The gas sensor element generally works with the solid electrolyte body heated to a high temperature (e.g., 500° C. or more) at which the solid electrolyte body can be activated. Therefore, when water drops included in the measurement gas come to adhere to the gas sensor element, a large thermal shock may be applied to the gas sensor element, thereby causing cracks to occur in the gas sensor element.

To solve the above problem, there is disclosed, for example in Japanese Patent Application Publications No. 2007-33374 and No. 2008-216241, a technique of covering the entire outer surface of the main body of the gas sensor element with a porous protective layer.

Specifically, according to the technique, the main body of the gas sensor element is first dipped in a slurry material for forming the protective layer. Consequently, the slurry material is applied on the entire outer surface of the main body of the gas sensor element. Then, the slurry material applied on the main body is dried and fired, thereby forming the protective layer.

However, with the above technique, it may be difficult to evenly apply the slurry material on the outer surface of the main body of the gas sensor element. More specifically, the main body of the gas sensor element is generally shaped so as to have a substantially rectangular cross section perpendicular to an axial direction (or a longitudinal direction) of the main body. Therefore, when the slurry material is applied on the outer surface of the main body by dipping, the thickness of the slurry material on the outer surface of the main body tends to be smaller at the corner portions of the main body than at the plane portions (or side surfaces) of the main body which extend between the corner portions. Consequently, the thickness of the resultant protective layer at the corner portions of the main body may be too small to reliably protect the main body from the water drops included in the measurement gas.

In addition, to secure a sufficiently large thickness of the protective layer at the corner portions of the main body, one may consider repeatedly applying the slurry material on the outer surface of the main body by dipping. However, in this case, the thickness of the protective layer is also increased at the plane portions of the main body, thereby increasing the heat capacity of the gas sensor element that includes the main body and the protective layer. Consequently, in operation of the gas sensor element, the time required for heating the solid electrolyte body to its activation temperature is accordingly increased, thereby making it difficult to ensure prompt activation of the solid electrolyte body.

SUMMARY

According to an exemplary embodiment, a gas sensor element is provided which has a main body that includes a solid electrolyte body, a measurement electrode, a reference electrode, a porous diffusion-resistant layer and a heater layer. The solid electrolyte body has oxygen ion conductivity and a pair of first and second surfaces that are opposite to each other in a lamination direction of the main body. The measurement electrode is provided on the first surface of the solid electrolyte body so as to be exposed to a measurement gas. The reference electrode is provided on the second surface of the solid electrolyte body so as to be exposed to a reference gas. The diffusion-resistant layer is laminated on the same side of the solid electrolyte body as the measurement electrode in the lamination direction of the main body so that the measurement gas is introduced to the measurement electrode through the diffusion-resistant layer. The heater layer is laminated on the same side of the solid electrolyte body as the reference electrode in the lamination direction of the main body and includes an electrical heating element that generates heat upon being supplied with electric power. The main body of the gas sensor element has a substantially rectangular cross section perpendicular to an axial direction of the main body; the axial direction is perpendicular to the lamination direction of the main body. The main body of the gas sensor element also has four plane portions and four corner portions each of which is formed between one adjacent pair of the plane portions. The four plane portions of the main body include a first pair of plane portions that are opposite to each other in the lamination direction of the main body and a second pair of plane portions that are opposite to each other in a direction perpendicular to both the lamination and axial directions of the main body. The four corner portions of the main body include a pair of first corner portions that are formed on the diffusion-resistant layer side in the lamination direction of the main body and a pair of second corner portions that are formed on the heater layer side in the lamination direction. At each of the first corner portions of the main body, the diffusion-resistant layer has a measurement gas inlet via which the measurement gas flows into the diffusion-resistant layer. The gas sensor element further includes a protective layer which is comprised of an inner protective layer that covers at least the first corner portions of the main body and an outer protective layer that covers the entire outer periphery of the main body and the inner protective layer. The protective layer has a larger average thickness at the first corner portions of the main body than at the plane portions of the main body.

That is, in the above gas sensor element, there is formed, at each of the first corner portions of the main body, one measurement gas inlet via which the measurement gas flows into the diffusion-resistant layer. Therefore, it is required for the gas sensor element to have high water resistance especially at the first corner portions of the main body.

With the above configuration of the gas sensor element, it is possible to secure a sufficiently large average thickness of the protective layer at the first corner portions of the main body, thereby reliably preventing the first corner portions from being damaged by water included in the measurement gas. In other words, it is possible to secure high water resistance of the gas sensor element at the first corner portions of the main body.

Moreover, with the above configuration, it is also possible to minimize the average thickness of the protective layer at the plane portions of the main body. As a result, it is possible to suppress increase in the heat capacity of the gas sensor element due to formation of the protective layer on the main body, thereby ensuring prompt activation of the solid electrolyte body.

According to a further implementation, the inner protective layer is made of first ceramic particles, and the outer protective layer is made of second ceramic particles. In this case, it is preferable that the first ceramic particles have a smaller average particle diameter than the second ceramic particles.

It is further preferable that the average particle diameter of the first ceramic particles is in the range of 2 to 14 µm, while the average particle diameter of the second ceramic particles is in the range of 14 to 35 µm.

Preferably, the inner protective layer has a smaller porosity than the outer protective layer.

It is further preferable that the porosity of the inner protective layer is in the range of 10 to 45%, while the porosity of the outer protective layer is in the range of 45 to 70%.

Preferably, the average thickness of the protective layer at the first corner portions of the main body is greater than or equal to 50 µm.

Further, it is also preferable that the average thickness of the protective layer at the first corner portions of the main body is less than or equal to 700 µm.

Preferably, the inner protective layer covers the second corner portions of the main body as well as the first corner portions; the protective layer has a larger average thickness at the second corner portions of the main body than at the plane portions of the main body.

It is further preferable that the average thickness of the protective layer at the first corner portions of the main body is larger than that at the second corner portions of the main body.

Preferably, each of the first corner portions of the main body is chamfered to have a chamfer surface or rounded to have a rounded surface; in the chamfer surface or the rounded surface, there is formed the measurement gas inlet of the diffusion-resistant layer.

It is further preferable that each of the second corner portions of the main body is also chamfered to have a chamfer surface or rounded to have a rounded surface.

According to the exemplary embodiment, there is also provided a method of manufacturing the gas sensor element. The method includes the steps of: (1) preparing the main body, a first material for forming the inner protective layer and a second material for forming the outer protective layer; (2) applying the first material on at least the first corner portions of the main body; (3) applying the second material to cover the entire outer periphery of the main body and the applied first material; and (4) heat-treating both the applied first and second materials to respectively form the inner and outer protective layers.

With the above method, it is possible to secure a sufficiently large average thickness of the protective layer at the first corner portions of the main body. At the same time, it is also possible to minimize the average thickness of the protective layer at the plane portions of the main body. Consequently, in the resultant gas sensor element, the first corner portions of the main body can be reliably prevented from being damaged by water included in the measurement gas; prompt activation of the solid electrolyte body can be ensured.

It is preferable that the first material is applied using a dispenser.

It is also preferable that the second material is applied by dipping.

Preferably, the first material has a higher viscosity than the second material.

It is further preferable that the viscosity of the first material is in the range of 1500 to 6000 mPa·s, while the viscosity of the second material is in the range of 100 to 1200 mPa·s.

According to the exemplary embodiment, there is also provided a gas sensor that includes the gas sensor element.

Since the gas sensor element has the above-described advantages, the gas sensor including the gas sensor element accordingly has both high durability and high performance.

BRIEF DESCRIPTION OF THE DRAWINGS

The present invention will be understood more fully from the detailed description given hereinafter and from the accompanying drawings of exemplary embodiments, which, however, should not be taken to limit the invention to the specific embodiments but are for the purpose of explanation and understanding only.

In the accompanying drawings:

FIG. 10A is a tabular representation showing the evaluation results of gas sensor element samples E1-E36 in an experiment;

FIG. 10B is a tabular representation showing the evaluation results of gas sensor element samples C1-C33 in the experiment;

DESCRIPTION OF EMBODIMENTS

Figure 1:
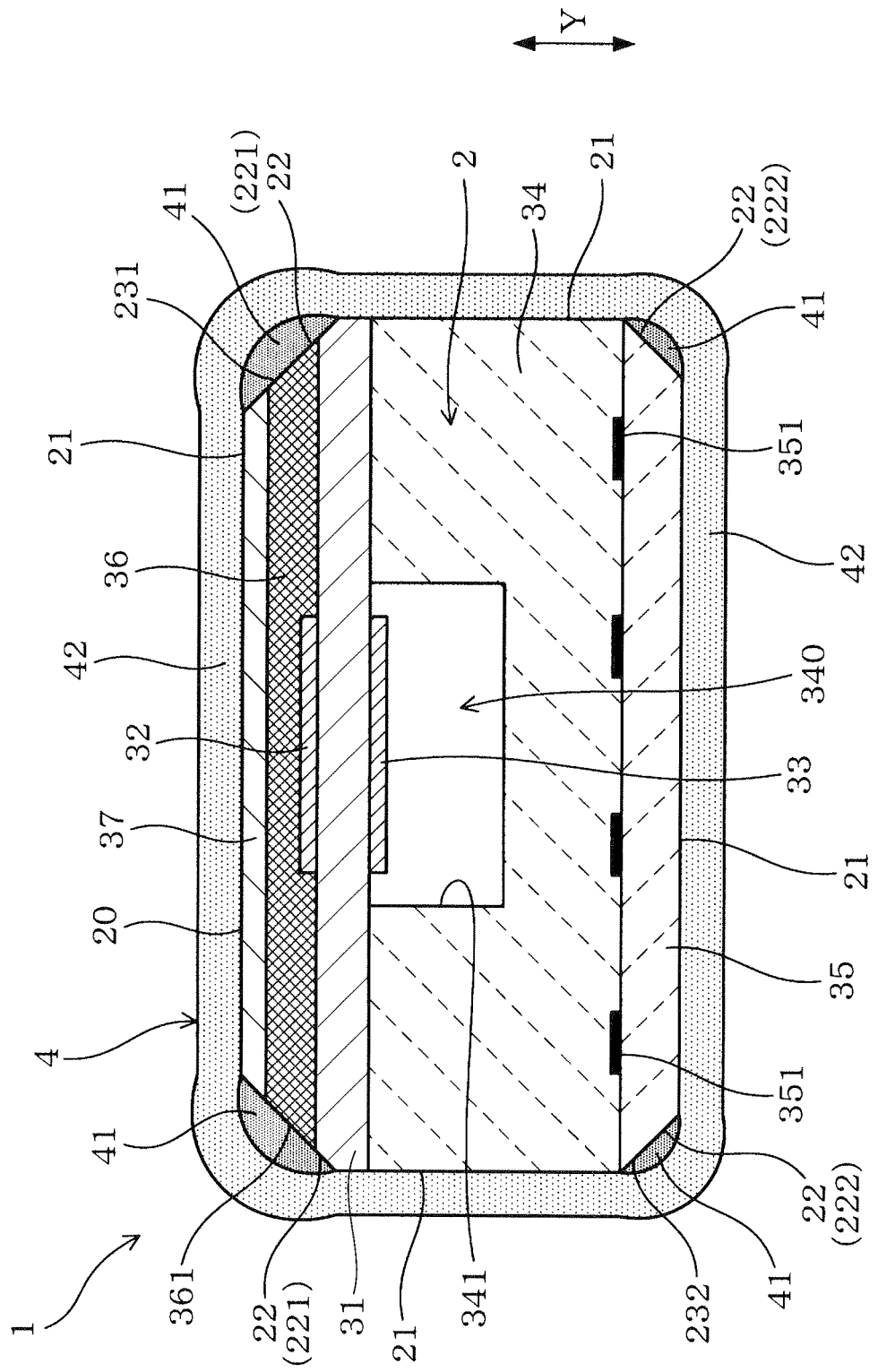
FIG. 1 is a cross-sectional view illustrating the overall configuration of a gas sensor element according to a first embodiment.

Exemplary embodiments will be described hereinafter with reference to FIGS. 1-18C. It should be noted that for the sake of clarity and understanding, identical components having identical functions in different embodiments have been marked, where possible, with the same reference numerals in each of the figures and that for the sake of avoiding redundancy, descriptions of the identical components will not be repeated.

First Embodiment

Figure 2:
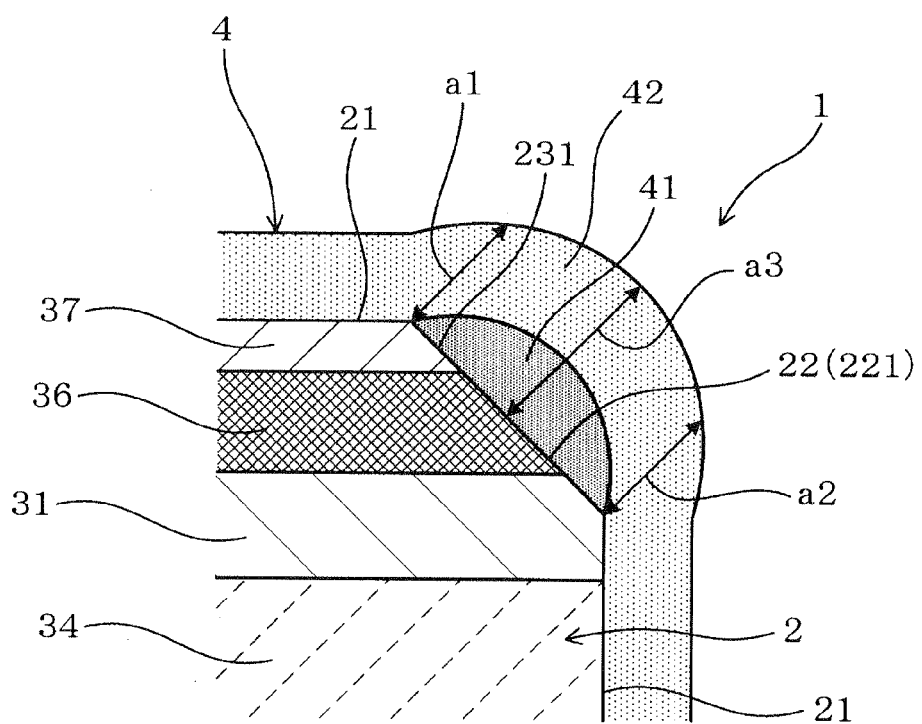
FIG. 2 is an enlarged view of an upper right corner portion of FIG. 1.

FIG. 1 illustrates the overall configuration of a gas sensor element 1 according to a first embodiment. FIG. 2 shows a corner portion of the gas sensor element 1.

As shown in FIGS. 1 and 2, the gas sensor element 1 has a main body 2 that includes a solid electrolyte body 31, a measurement electrode 32, a reference electrode 33, a heater layer 35, and a porous diffusion-resistant layer 36. The solid electrolyte body 31 has oxygen ion conductivity and a pair of first and second surfaces (i.e., the upper and lower surfaces in FIG. 1) that are opposite to each other in a lamination direction Y of the main body 2. The measurement electrode 32 is provided on the first surface of the solid electrolyte body 31 so as to be exposed to a measurement gas (i.e., a gas to be measured). The reference electrode 33 is provided on the second surface of the solid electrolyte body 31 so as to be exposed to a reference gas. The heater layer 35 is laminated on the same side of the solid electrolyte body 31 as the reference electrode 33 in the lamination direction Y (i.e., on the lower side of the solid electrolyte body 31 in FIG. 1) and includes an electrical heating element 351 that generates heat upon being supplied with electric power. The diffusion-resistant layer 36 is laminated on the same side of the solid electrolyte body 31 as the measurement electrode 32 in the lamination direction Y (i.e., on the upper side of the solid electrolyte body 31 in FIG. 1) so that the measurement gas is introduced to the measurement electrode 32 through the diffusion-resistant layer 36.

Figure 3A:
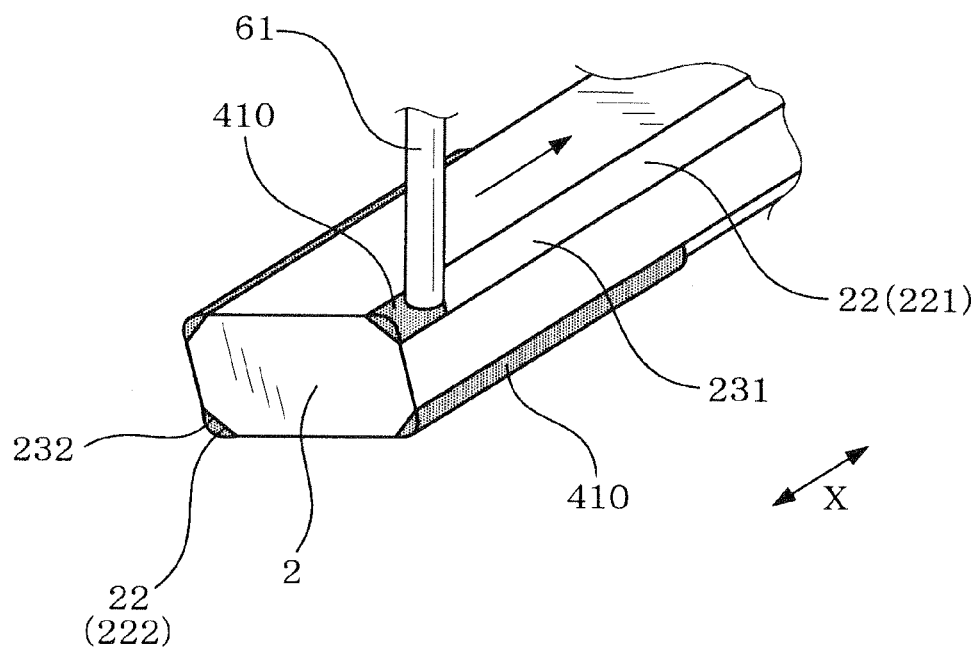
FIGS. 3A and 3B are schematic perspective views illustrating a first application step of a method of manufacturing the gas sensor element according to the first embodiment.
Figure 3B:
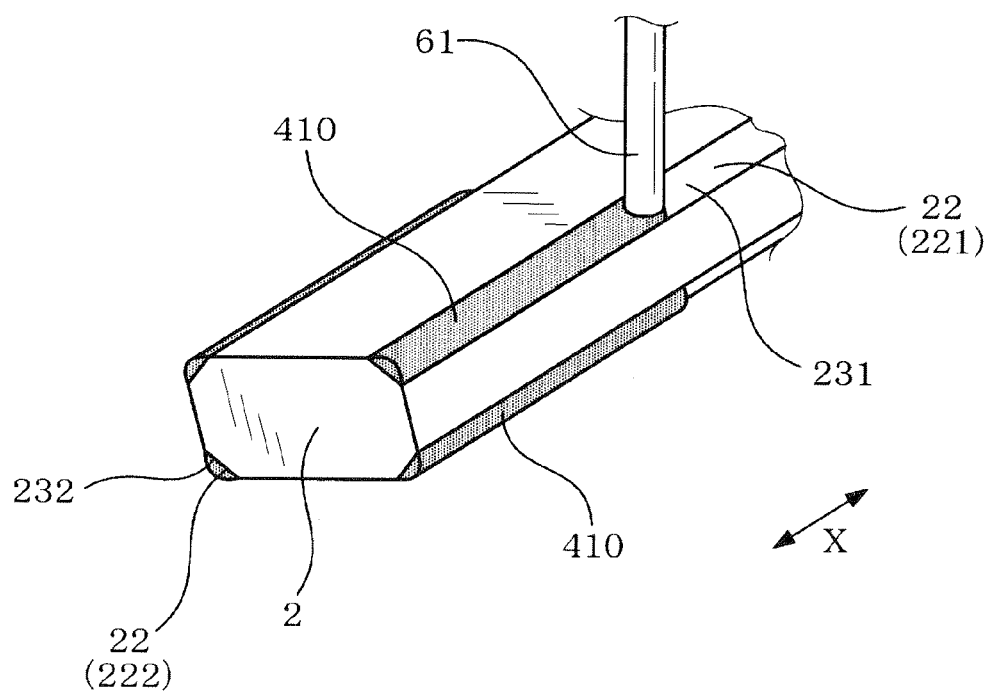

In the present embodiment, the main body 2 of the gas sensor element 1 is shaped so as to have a substantially rectangular cross section perpendicular to an axial direction (or a longitudinal direction) X of the main body 2; the axial direction X is perpendicular to the lamination direction Y of the main body 2. In addition, the axial direction X of the main body 2 is shown in FIGS. 3A and 3B and coincides with the direction perpendicular to the paper surface of FIG. 1.

Accordingly, the main body 2 of the gas sensor element 1 has a first pair of plane portions (or side surfaces) 21 that are opposite to each other in the lamination direction Y of the main body 2 and a second pair of plane portions (or side surfaces) 21 that are opposite to each other in a direction perpendicular to both the axial direction X and lamination direction Y of the main body 2.

The main body 2 of the gas sensor element 1 also has four corner portions 22 each of which is formed between one adjacent pair of the plane portions 21 of the main body 2. More specifically, the four corner portions 22 of the main body 2 include a pair of first corner portions 221 that are formed on the diffusion-resistant layer 36 side in the lamination direction Y of the main body 2 and a pair of second corner portions 222 that are formed on the heater layer 35 side in the lamination direction Y. In addition, at each of the first corner portions 221 of the main body 2, the diffusion-resistant layer 36 has a measurement gas inlet 361 via which the measurement gas flows into the diffusion-resistant layer 36.

In the present embodiment, the gas sensor element 1 further includes a protective layer 4 that is comprised of an inner protective layer 41 and an outer protective layer 42. The inner protective layer 41 is formed on the main body 2 of the gas sensor element 1 so as to cover only the four corner portions 22 of the main body 2. The outer protective layer 42 is formed on both the main body 2 and the inner protective layer 41 so as to cover the entire outer periphery of the main body 2 and the inner protective layer 41. In other words, the outer protective layer 42 is formed so as to cover the entire outer periphery of a unit that is comprised of the main body 2 and the inner protective layer 41 formed on the main body 2. Further, the protective layer 4 has a larger average thickness at the corner portions 22 of the main body 2 than at the plane portions 21 of the main body 2.

The configuration of the gas sensor element 1 according to the present embodiment will be described in more detail hereinafter.

In the present embodiment, the gas sensor element 1 is configured as an A/F (Air/Fuel) ratio sensor element to sense the A/F ratio of air-fuel mixture supplied to an internal combustion engine of a motor vehicle. More specifically, in this case, the A/F ratio is determined based on the limit current of the gas sensor element 1 flowing between the measurement and reference electrodes 32 and 33; the limit current depends on the concentration of oxygen in the exhaust gas from the engine.

That is, in the present embodiment, the measurement gas is the exhaust gas from the engine, and the reference gas is air.

The gas sensor element 1 has the main body 2 in which the measurement and reference electrodes 32 and 33 are respectively provided on the first and second surfaces of the solid electrolyte body 31 that has oxygen ion conductivity. The solid electrolyte body 31 is made of, for example, zirconia. Both the measurement and reference electrodes 32 and 33 are made of for example, platinum (Pt).

The main body 2 of the gas sensor element 1 further includes a reference gas chamber formation layer 34 and a shield layer 37 in addition to the solid electrolyte body 31, the measurement and reference electrodes 32 and 33, the heater layer 35 and the diffusion-resistant layer 36.

The reference gas chamber formation layer 34 is laminated on the second surface of the solid electrolyte body 31 around the reference electrode 33. The reference gas chamber formation layer 34 is made of, for example, dense alumina that is gas impermeable and electrically insulative. In that surface of the reference gas chamber formation layer 34 which abuts the second surface of the solid electrolyte body 31, there is formed a groove 341 that makes up a reference gas chamber 340. The reference electrode 33 is positioned within the reference gas chamber 340. In operation, the reference gas chamber 340 is filled with the reference gas which is introduced into the chamber 340 via an opening (not shown) of the chamber 340; consequently, the reference electrode 33 is exposed to the reference gas.

On that surface of the reference gas chamber formation layer 34 which is on the opposite side to the solid electrolyte body 31 in the lamination direction Y, there is laminated the heater layer 35. The electrical heating element 351 is provided in the heater layer 35 so as to face the reference gas chamber formation layer 34. In operation, the heating element 351 is supplied with electric power to generate heat, thereby heating the gas sensor element 1 to the activation temperature of the solid electrolyte layer 31.

The diffusion-resistant layer 36 is laminated on the first surface of the solid electrolyte body 31 so as to cover the measurement electrode 32. The diffusion-resistant layer 36 is made of, for example, gas-permeable porous alumina.

The diffusion-resistant layer 36 has a pair of plane portions 361 that are opposite to each other in the direction perpendicular to both the axial direction X and lamination direction Y of the main body 2 and make up the measurement gas inlets 361 of the diffusion-resistant layer 36. The measurement gas is first introduced into the diffusion-resistant layer 36 via the measurement gas inlets 361 and then flows, through the inside of the diffusion-resistant layer 36, to the measurement electrode 32. Consequently, the measurement electrode 32 is exposed to the measurement gas.

On that surface of the diffusion-resistant layer 36 which is on the opposite side to the solid electrolyte body 31 in the lamination direction Y, there is laminated the shield layer 37. The shield layer 37 is made of, for example, dense alumina that is gas impermeable and electrically insulative.

As shown in FIGS. 1 and 2, the main body 2 of the gas sensor element 1 has the substantially rectangular cross section perpendicular to the axial direction X thereof.

The main body 2 of the gas sensor element 1 has the first pair of plane portions 21 that are opposite to each other in the lamination direction Y of the main body 2 and the second pair of plane portions 21 that are opposite to each other in the direction perpendicular to both the axial direction X and lamination direction Y of the main body 2.

The main body 2 of the gas sensor element 1 also has the four corner portions 22 each of which is formed between one adjacent pair of the plane portions 21 of the main body 2. The four corner portions 22 include the pair of first corner portions 221 formed on the diffusion-resistant layer 36 side and the pair of second corner portions 222 formed on the heater layer 35 side in the lamination direction Y of the main body 2. In addition, at each of the first corner portions 221 of the main body 2, there is formed one measurement gas inlet 361 of the diffusion-resistant layer 36.

Furthermore, in the present embodiment, each of the first corner portions 221 of the main body 2 is chamfered at, for example, 45° to have a chamfer surface 231. The dimension of the chamfer surface 231 is set to be, for example, in the range of 0.1 to 0.6 mm. In addition, in the chamfer surface 231, there is formed the measurement gas inlet 361 of the diffusion-resistant layer 36.

Similarly, each of the second corner portions 222 of the main body 2 is also chamfered at, for example, 45° to have a chamfer surface 232. The dimension of the chamfer surface 232 is set to be, for example, 0.3 mm.

The gas sensor element 1 further includes the protective layer 4 that is comprised of the inner and outer protective layers 41 and 42. The inner protective layer 41 is formed on the main body 2 of the gas sensor element 1 so as to cover only the four corner portions 22 (i.e., the first corner portions 221 and the second corner portions 222) of the main body 2. The outer protective layer 42 is formed on both the main body 2 and the inner protective layer 41 so as to cover the entire outer periphery of the main body 2 and the inner protective layer 41.

The inner protective layer 41 is configured as a porous layer the porosity of which is in the range of 10 to 45%. The inner protective layer 41 is made of, for example, alumina particles which have an average particle diameter in the range of 2 to 14 μm. On the other hand, the outer protective layer 42 is configured as a porous layer the porosity of which is in the range of 45 to 70%. The outer protective layer 42 is made of, for example, alumina particles which have an average particle diameter in the range of 14 to 35 μm.

That is, in the present embodiment, the average particle diameter of the alumina particles forming the inner protective layer 41 is less than that of the alumina particles forming the outer protective layer 42. Further, the porosity of the inner protective layer 41 is less than that of the outer protective layer 42.

Moreover, in the present embodiment, each of the corner portions 22 of the main body 2 is covered by both the inner and outer protective layers 41 and 42, while each of the plane portions 21 of the main body 2 is covered by only the outer protective layer 42. Consequently, it is possible to allow the protective layer 4 to have a larger average thickness at the corner portions 22 of the main body 2 than at the plane portions 21 of the main body 2.

Specifically, in the present embodiment, the protective layer 4 has an average thickness of 400 μm at each of the plane portions 21 of the main body 2, an average thickness of 650 m at each of the first corner portions 221 of the main body 2, and an average thickness of 550 μm at each of the second corner portions 222 of the main body 2.

For each of the first corner portions 221 of the main body 2, the average thickness of the protective layer 4 at the first corner portion 221 is determined by first measuring values of the thickness of the protective layer 4 in a direction perpendicular to the chamfer surface 231 of the first corner portion 221 at a plurality of points on the chamfer surface 231 and then taking an average of all the measured values of the thickness of the protective layer 4.

More specifically, in the present embodiment, as shown in FIG. 2, the average thickness of the protective layer 4 at the first corner portion 221 is determined by: (1) measuring a value a1 of the thickness of the protective layer 4 at the shield layer 37–side end of the chamfer surface 231 of the first corner portion 221, a value a2 of the thickness at the solid electrolyte body 31–side end of the chamfer surface 231, and a value a3 of the thickness at the middle between the shield layer 37–side end and the solid electrolyte body 31–side end of the chamfer surface 231; and (2) taking an average of all the measured values a1-a3 of the thickness of the protective layer 4.

Similarly, for each of the second corner portions 222 of the main body 2, the average thickness of the protective layer 4 at the second corner portion 222 is determined by first measuring values of the thickness of the protective layer 4 in a direction perpendicular to the chamfer surface 232 of the second corner portion 222 at a plurality of points on the chamfer surface 232 and then taking an average of all the measured values of the thickness of the protective layer 4.

As to the details of determining the average thickness of the protective layer 4 at the second corner portions 222, they are similar to the above-described details of determining the average thickness of the protective layer 4 at the first corner portions 221, and thus not described hereinafter.

On the other hand, for each of the plane portions 21 of the main body 2, the average thickness of the protective layer 4 at the plane portion 21 is determined by first measuring values of the thickness of the protective layer 4 in a direction perpendicular to the plane portion 21 at a plurality of points on the plane portion 21 and then taking an average of all the measured values of the thickness of the protective layer 4.

In addition, in the present embodiment, the entire outer surface 20 of the main body 2, which includes the plane portions 21 and the outer surfaces of the corner portions 22, is covered by the protective layer 4.

After having described the configuration of the gas sensor element 1, a method of manufacturing it according to the present embodiment will be described hereinafter.

In the present embodiment, the method of manufacturing the gas sensor element 1 includes a preparing step, a first application step, a second application step and a heat treatment step.

In the preparing step, the main body 2, a first material 410 for forming the inner protective layer 41 and a second material 420 for forming the outer protective layer 42 are prepared.

More specifically, in this step, ceramic sheets for respectively forming the heater layer 35, the reference gas chamber formation layer 34, the solid electrolyte body 31, the diffusion-resistant layer 36 and the shield layer 37 are sequentially laminated in the lamination direction Y to form a laminate. Then, the laminate is fired at 1400 to 1500° C. for one to three hours, thereby forming the main body 2.

Further, in this step, alumina particles with an average particle diameter in the range of 2 to 14 μm, an inorganic binder and water are mixed and kneaded, thereby obtaining the first material 410 in the form of paste. In addition, the obtained first material 410 has a viscosity in the range of 1500 to 6000 mPa·s.

Moreover, in this step, alumina particles with an average particle diameter in the range of 14 to 35 μm, an inorganic binder and water are mixed and kneaded, thereby obtaining the second material 420 in the form of slurry. In addition, the obtained second material 420 has a viscosity in the range of 100 to 1200 mPa·s.

In the first application step, as shown in FIGS. 3A and 3B, the first material 410 is applied, using a dispenser (or a fixed-quantity liquid discharger) 61, only on the four corner portions 22 (i.e., the first and second corner portions 221 and 222) of the main body 2. Consequently, each of the four corner portions 22 of the main body 2 is covered with the first material 410.

Figure 4A:
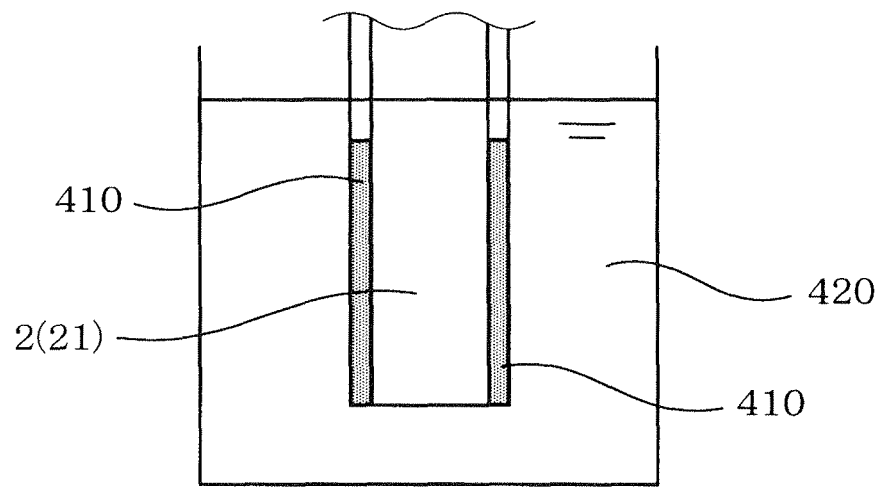
FIGS. 4A and 4B are schematic perspective views illustrating a second application step of the method.
Figure 4B:
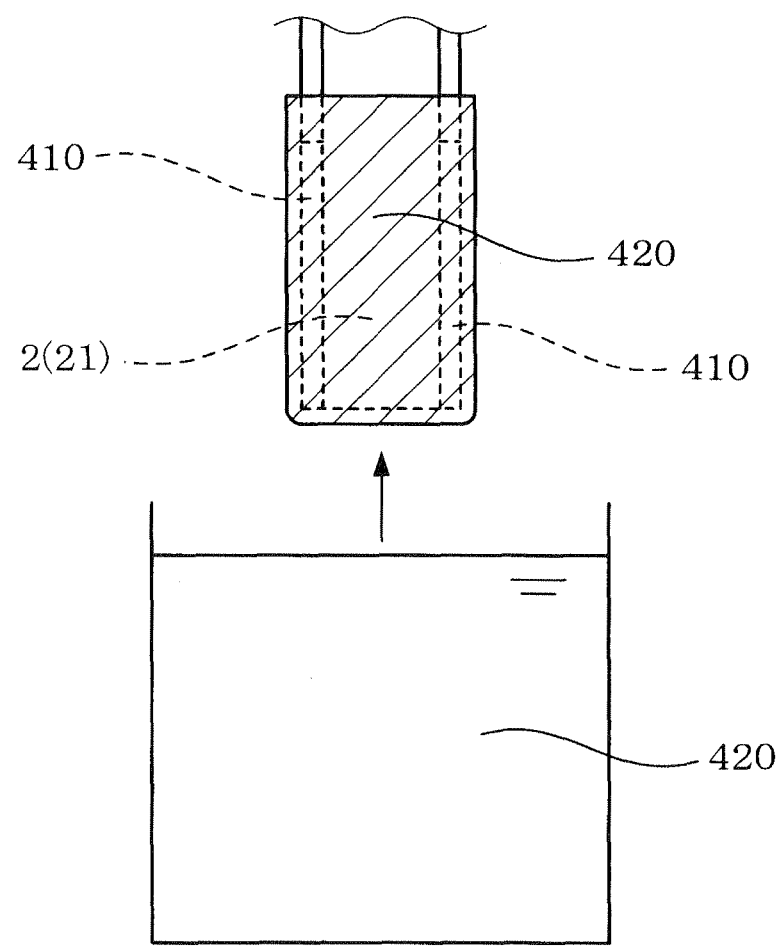

In the second application step, as shown in FIG. 4A, the main body 2, which has the first material 410 applied thereon, is first dipped into the second material 420. Then, as shown in FIG. 4B, the main body 2 is raised out of the second material 420. Consequently, the second material 420 is applied on both the main body 2 and the first material 410 to cover the entire outer periphery of the main body 2 and the first material 410. In other words, the second material 420 is applied to cover the entire outer periphery of a unit that is comprised of the main body 2 and the first material 410 applied on the main body 2.

In the heat treatment step, the main body 2, which has both the first and second materials 410 and 420 applied thereon, is heated at 800 to 1000° C. for one to two hours. Consequently, both the first and second materials 410 and 420 are dried and fired, thereby respectively forming the inner and outer protective layers 41 and 42 on the main body 2.

As a result, the gas sensor element 1 according to the present embodiment is obtained.

Figure 5:
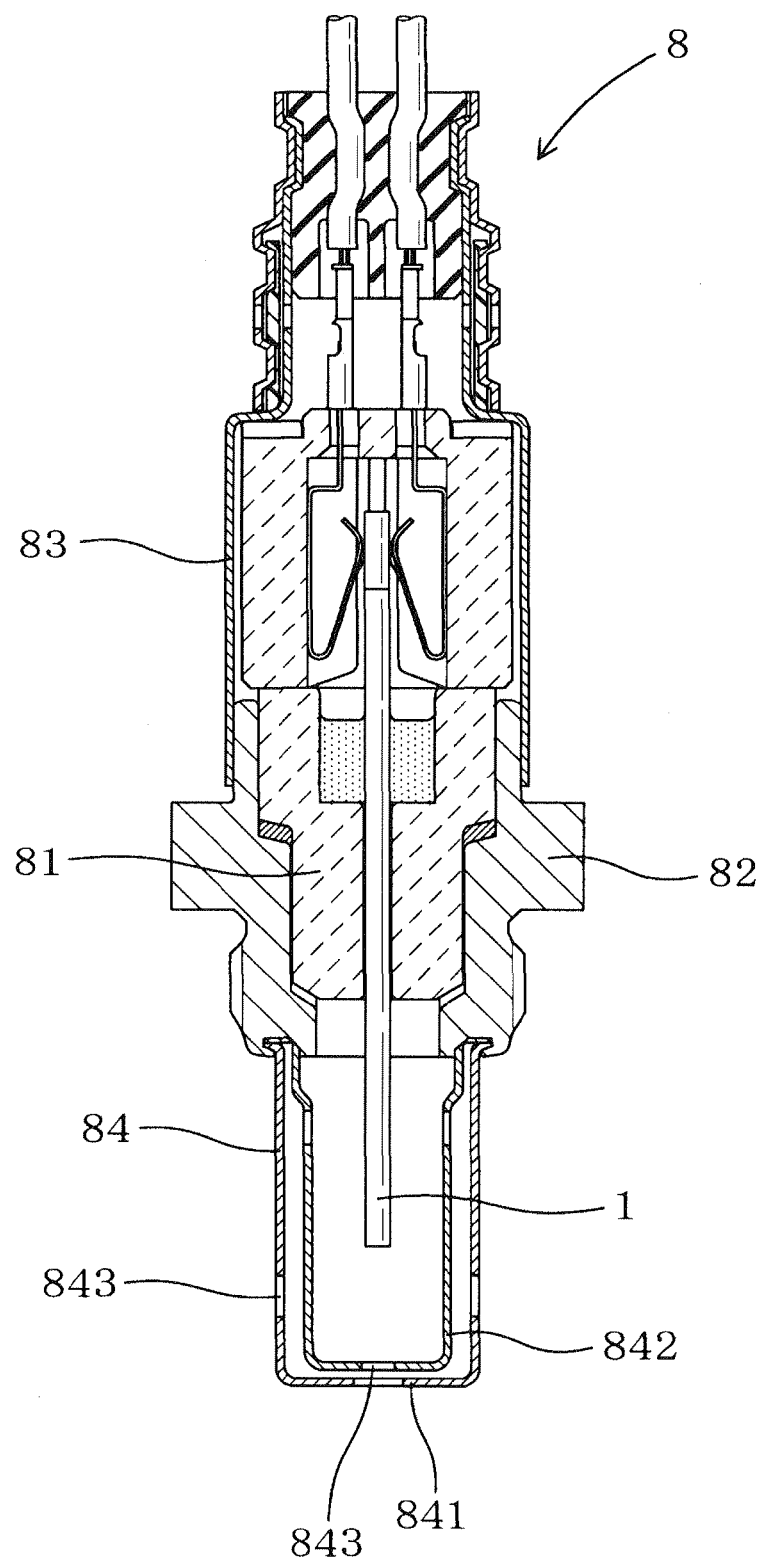
FIG. 5 is a cross-sectional view of a gas sensor that includes the gas sensor element according to the first embodiment.

Next, a gas sensor 8 which has the gas sensor element 1 incorporated therein will be described with reference to FIG. 5.

The gas sensor 8 includes, in addition to the gas sensor element 1, an insulator 81, a housing 82, a base-side cover 83, and a tip-side cover 84. The insulator 81 has the gas sensor element 1 partially inserted and held therein. The housing 82 has the insulator 81 partially inserted and held therein. The base-side cover 83 is fixed to a base end (i.e., the upper end in FIG. 5) of the housing 82 to protect that part of the insulator 81 which protrudes from the base end of the housing 81. The tip-side cover 84 is fixed to a tip end (i.e., the lower end in FIG. 5) of the housing 82 to protect that part of the gas sensor element 1 which protrudes from the tip end of the housing 82. The tip-side cover 84 is a double cover consisting of an outer cover 841 and an inner cover 842. Each of the inner and outer covers 841 and 842 has through-holes 843 formed through its end and side walls. In operation of the gas sensor 8, the measurement gas is introduced to the gas sensor element 1 through the through-holes 843 of the inner and outer covers 841 and 842.

According to the present embodiment, it is possible to achieve the following advantages.

As described above, in the present embodiment, the main body 2 of the gas sensor element 1 has the substantially rectangular cross section perpendicular to the axial direction X of the main body 2. The main body 2 also has the four plane portions 21 and the four corner portions 22 each of which is formed between one adjacent pair of the plane portions 21. The four plane portions 21 of the main body 2 include the first pair of plane portions 21 that are opposite to each other in the lamination direction Y of the main body 2 and the second pair of plane portions 21 that are opposite to each other in the direction perpendicular to both the lamination direction Y and the axial direction X. The four corner portions 22 of the main body 2 include the pair of first corner portions 221 that are formed on the diffusion-resistant layer 36 side in the lamination direction Y of the main body 2 and the pair of second corner portions 222 that are formed on the heater layer 35 side in the lamination direction Y. At each of the first corner portions 221 of the main body 2, the diffusion-resistant layer 36 has the measurement gas inlet 361 via which the measurement gas flows into the diffusion-resistant layer 36. The gas sensor element 1 also includes the protective layer 4 which is comprised of the inner protective layer 41 that covers only the four corner portions 22 of the main body 2 and the outer protective layer 42 that covers the entire outer periphery of the main body 2 and the inner protective layer 41. The average thickness of the protective layer 4 at the first corner portions 221 of the main body 2 is greater than that at the plane portions 21 of the main body 2.

That is, in the gas sensor element 1, there is formed, at each of the first corner portions 221 of the main body 2, one measurement gas inlet 361 via which the measurement gas flows into the diffusion-resistant layer 36. Therefore, it is required for the gas sensor element 1 to have high water resistance especially at the first corner portions 221 of the main body 2.

With the above configuration of the gas sensor element 1 according to the present embodiment, each of the first corner portions 221 of the main body 2 is covered by both the inner and outer protective layers 41 and 42 of the protective layer 4. Consequently, it becomes possible to secure a sufficiently large average thickness of the protective layer 4 at the first corner portions 221 of the main body 2, thereby reliably preventing the first corner portions 221 from being damaged by water included in the measurement gas. In other words, it becomes possible to secure high water resistance of the gas sensor element 1 at the first corner portions 221 of the main body 2.

On the other hand, each of the plane portions 21 of the main body 2 is covered by only the outer protective layer 42 of the protective layer 4. Consequently, it becomes possible to minimize the average thickness of the protective layer 4 at the plane portions 21 of the main body 2. As a result, it becomes possible to suppress increase in the heat capacity of the gas sensor element 1 due to formation of the protective layer 4 on the main body 2, thereby ensuring prompt activation of the solid electrolyte body 31.

In the present embodiment, the average particle diameter of the alumina particles forming the inner protective layer 41 is smaller than that of the alumina particles forming the outer protective layer 42.

As described above, the inner protective layer 41 covers the first corner portions 221 of the main body 2; at each of the first corner portions 221, there is formed one measurement gas inlet 361 of the diffusion-resistant layer 36. Therefore, with the smaller average particle diameter of the alumina particles forming the inner protective layer 41, it is possible to reliably prevent water included in the measurement gas from intruding into the measurement gas inlets 361 of the diffusion-resistant layer 36 formed at the first corner portions 221 of the main body 2. Moreover, with the smaller average particle diameter, it is also possible to improve adhesion of the inner protective layer 41 to the main body 2.

Further, in the present embodiment, the average particle diameter of the alumina particles forming the inner protective layer 41 is in the range of 2 to 14 μm, and the average particle diameter of the alumina particles forming the outer protective layer 42 is in the range of 14 to 35 μm.

Setting the average particle diameter of the alumina particles forming the inner protective layer 41 in the range of 2 to 14 μm, it is possible to more reliably prevent water included in the measurement gas from intruding into the measurement gas inlets 361 of the diffusion-resistant layer 36 formed at the first corner portions 221 of the main body 2. Moreover, it is also possible to further improve adhesion of the inner protective layer 41 to the main body 2. On the other hand, setting the average particle diameter of the alumina particles forming the outer protective layer 42 in the range of 14 to 35 μm, when water included in the measurement gas has intruded into the outer protective layer 42, it is possible to effectively disperse the water in the outer protective layer 42, thereby vaporizing the water in a short time. As a result, it is possible to further enhance the water resistance of the gas sensor element 1.

In the present embodiment, the porosity of the inner protective layer 41 is smaller than that of the outer protective layer 42.

With the smaller porosity of the inner protective layer 41, it is possible to reliably prevent water included in the measurement gas from intruding into the measurement gas inlets 361 of the diffusion-resistant layer 36 formed at the first corner portions 221 of the main body 2. Moreover, with the smaller porosity, it is also possible to improve adhesion of the inner protective layer 41 to the main body 2.

Further, in the present embodiment, the porosity of the inner protective layer 41 is in the range of 10 to 45%, and the porosity of the outer protective layer 42 is in the range of 45 to 70%.

Setting the porosity of the inner protective layer 41 in the range of 10 to 45%, it is possible to more reliably prevent water included in the measurement gas from intruding into the measurement gas inlets 361 of the diffusion-resistant layer 36 formed at the first corner portions 221 of the main body 2. Moreover, it is also possible to further improve adhesion of the inner protective layer 41 to the main body 2. On the other hand, setting the porosity of the outer protective layer 42 in the range of 45 to 70%, when water included in the measurement gas has intruded into the outer protective layer 42, it is possible to effectively disperse the water in the outer protective layer 42, thereby vaporizing the water in a short time. As a result, it is possible to further enhance the water resistance of the gas sensor element 1.

In the present embodiment, the average thickness of the protective layer 4 at the first corner portions 221 of the main body 2 is equal to 650 μm.

Setting the average thickness of the protective layer 4 at the first corner portions 221 as above, it is possible to reliably prevent the first corner portions 221 from being damaged by water included in the measurement gas while ensuring prompt activation of the solid electrolyte body 31.

In addition, if the average thickness of the protective layer 4 at the first corner portions 221 was less than 50 μm, it would be difficult to reliably prevent the first corner portions 221 from being damaged by water included in the measurement gas. On the other hand, if the average thickness of the protective layer 4 at the first corner portions 221 was greater than 700 μm, it would be difficult to ensure prompt activation of the solid electrolyte body 31. Therefore, it is preferable that the average thickness of the protective layer 4 at the first corner portions 221 is in the range of 50 to 700 μm.

In the present embodiment, the inner protective layer 41 covers the second corner portions 222 of the main body 2 as well as the first corner portions 221. Moreover, the average thickness of the protective layer 4 at the second corner portions 222 of the main body 2 is larger than that at the plane portions 21 of the main body 2.

With the above configuration, it is possible to secure a sufficiently large average thickness of the protective layer 4 at the second corner portions 222 of the main body 2, thereby reliably preventing the second corner portions 22 from being damaged by water included in the measurement gas. In other words, it is possible to secure high water resistance of the gas sensor element 1 at the second corner portions 222 of the main body 2 as well as at the first corner portions 221 of the main body 2.

Further, in the present embodiment, the average thickness of the protective layer 4 at the first corner portions 221 of the main body 2 is larger than that at the second corner portions 222 of the main body 2.

Consequently, with the larger average thickness at the first corner portions 221, it is possible to reliably prevent water included in the measurement gas from intruding into the measurement gas inlets 361 of the diffusion-resistant layer 36 formed at the first corner portions 221. On the other hand, with the smaller average thickness at the second corner portions 222, it is possible to suppress increase in the heat capacity of the gas sensor element 1 due to formation of the protective layer 4 on the main body 2, thereby ensuring prompt activation of the solid electrolyte body 31.

In the present embodiment, each of the first corner portions 221 of the main body 2 is chamfered to have the chamfer surface 231, in which is formed the measurement gas inlet 361 of the diffusion-resistant layer 36.

Consequently, by chamfering the first corner portions 221 of the main body 2, it becomes easy to secure a sufficiently large average thickness of the protective layer 4 at the first corner portions 221, thereby reliably preventing the first corner portions 221 from being damaged by water included in the measurement gas.

Further, in the present embodiment, each of the second corner portions 222 of the main body 2 is also chamfered to have the chamfer surface 232.

Consequently, by chamfering the second corner portions 222 of the main body 2, it becomes easy to secure a sufficiently large average thickness of the protective layer 4 at the second corner portions 222, thereby reliably preventing the second corner portions 222 from being damaged by water included in the measurement gas.

In the present embodiment, the method of manufacturing the gas sensor element 1 includes the preparing step, the first application step, the second application step and the heat treatment step. In the preparing step, the main body 2, the first material 410 for forming the inner protective layer 41 and the second material 420 for forming the outer protective layer 42 are prepared. In the first application step, the first material 410 is applied only on the four corner portions 22 of the main body 2. In the second application step, the second material 420 is applied on both the main body 2 and the first material 410 applied on the main body 2, so as to cover the entire outer periphery of the main body 2 and the first material 410. In the heat treatment step, both the applied first and second materials 410 and 420 are heat-treated to respectively form the inner and outer protective layers 41 and 42.

With the above method, it is possible to secure a sufficiently large average thickness of the protective layer 4 at the first corner portions 221 of the main body 2. At the same time, it is also possible to minimize the average thickness of the protective layer 4 at the plane portions 21 of the main body 2. Consequently, in the resultant gas sensor element 1, the first corner portions 221 of the main body 2 can be reliably prevented from being damaged by water included in the measurement gas; prompt activation of the solid electrolyte body 31 can be ensured.

Moreover, in the present embodiment, in the first application step, the first material 410 is applied using the dispenser (or fixed-quantity liquid discharger) 61. Consequently, it is possible to accurately apply the first material 410 on the corner portions 22 of the main body 2.

Further, in the second application step, the second material 420 is applied by dipping. Consequently, it is possible to easily apply the second material 420 on both the main body 2 and the first material 410 applied on the main body 2, thereby covering the entire outer periphery of the main body 2 and the first material 410 with the second material 420.

In the present embodiment, the viscosity of the first material 410 is higher than that of the second material 420. More specifically, the viscosity of the first material 410 is in the range of 1500 to 6000 mPa·s, while the viscosity of the second material 420 is in the range of 100 to 1200 mPa·s.

Consequently, with the higher viscosity of the first material 410, it is possible to accurately apply the first material 410 only on the corner portions 22 of the main body 2 and retain the shape of the first material 410 on the corner portions 22.

On the other hand, with the lower viscosity of the second material 420, it is possible to easily apply the second material 420 on both the main body 2 and the first material 410 applied on the main body 2, thereby covering the entire outer periphery of the main body 2 and the first material 410 with the second material 420.

In the present embodiment, the gas sensor 8 includes the gas sensor element 1 having the above-described advantages. Accordingly, the gas sensor 8 has both high durability and high performance.

Second Embodiment

This embodiment illustrates a gas sensor element 1 which has a similar configuration to the gas sensor element 1 according to the first embodiment; accordingly, only the differences therebetween will be described hereinafter.

In the first embodiment, the inner protective layer 41 is formed on the main body 2 of the gas sensor element 1 so as to cover all the four corner portions 22 (i.e., the pair of first corner portions 221 and the pair of second corner portions 222) of the main body 2 (see FIG. 1).

Figure 6:
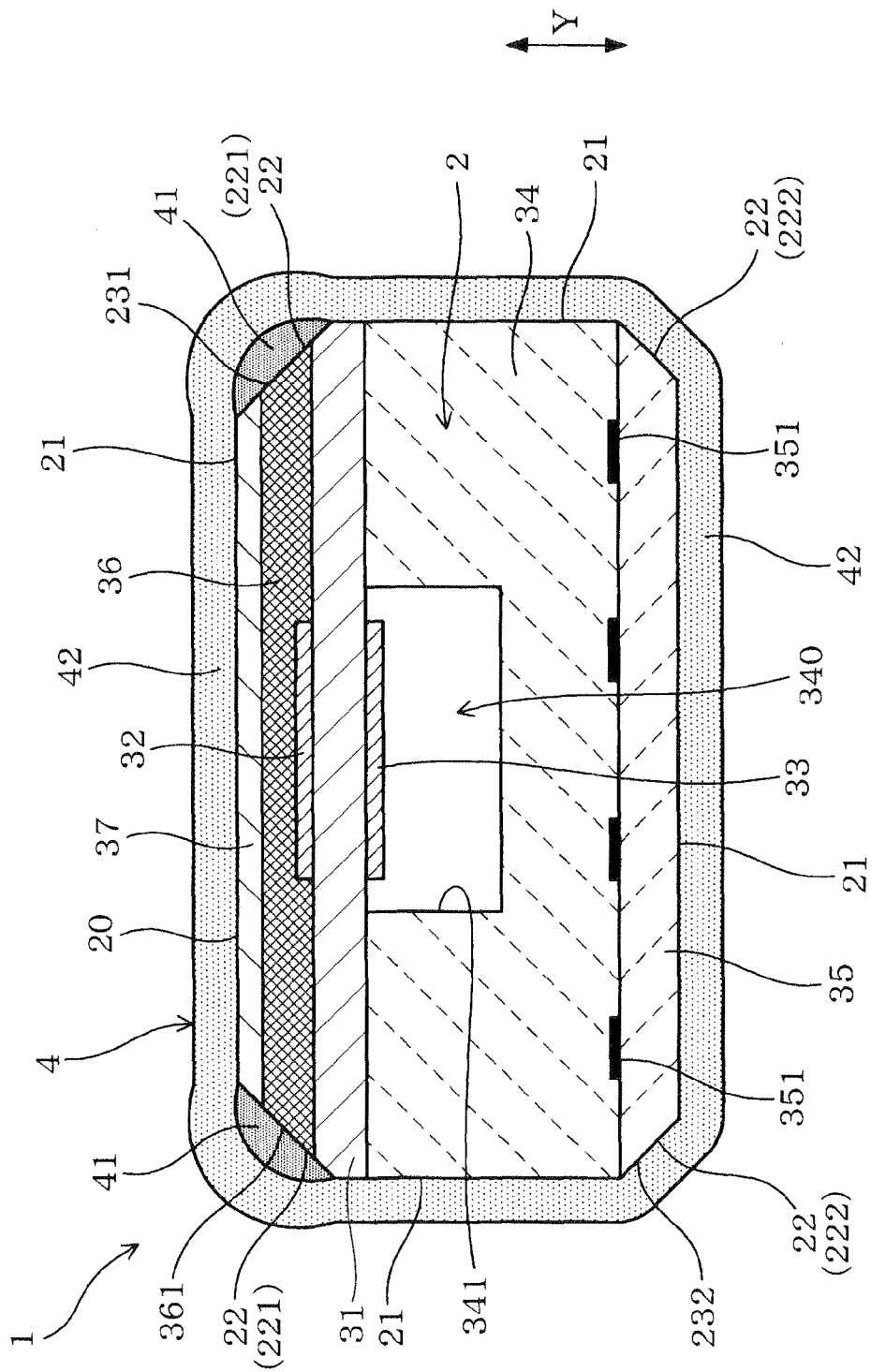
FIG. 6 is a cross-sectional view illustrating the overall configuration of a gas sensor element according to a second embodiment.

In comparison, in the present embodiment, as shown in FIG. 6, the inner protective layer 41 is formed on the main body 2 of the gas sensor element 1 so as to cover only the first corner portions 221 of the main body 2. That is, in the present embodiment, each of the second corner portions 222 of the main body 2 has no inner protective layer 41 formed thereon.

With the above configuration of the gas sensor element 1 according to the present embodiment, it is also possible to reliably prevent the first corner portions 221 of the main body 2 from being damaged by water included in the measurement gas while ensuring prompt activation of the solid electrolyte body 31.

Third Embodiment

This embodiment illustrates a gas sensor element 1 which has a similar configuration to the gas sensor element 1 according to the first embodiment; accordingly, only the differences therebetween will be described hereinafter.

In the first embodiment, each of the first corner portions 221 of the main body 2 is chamfered to have the chamfer surface 231; each of the second corner portions 222 of the main body 2 is also chamfered to have the chamfer surface 232 (see FIG. 1).

Figure 7:
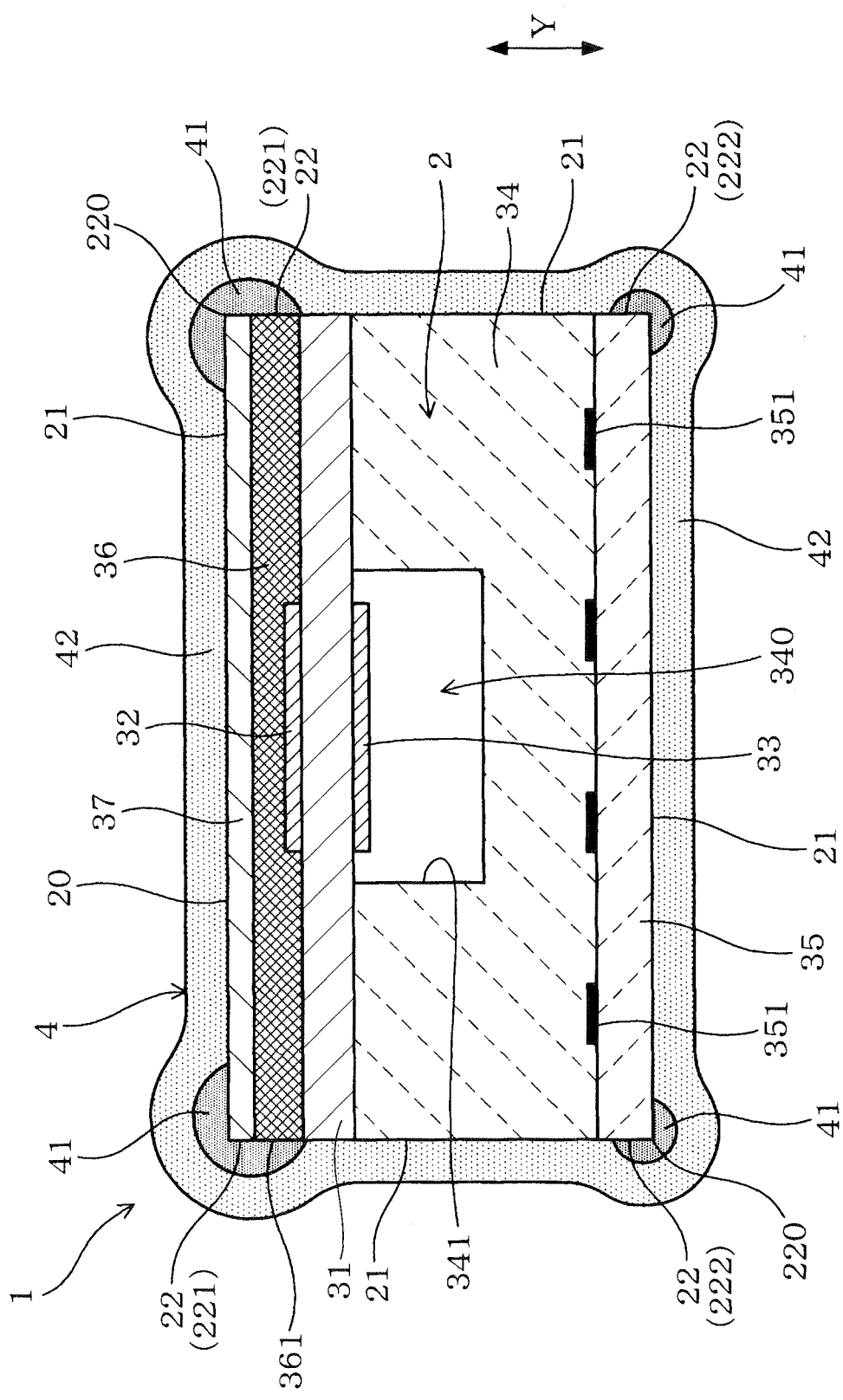
FIG. 7 is a cross-sectional view illustrating the overall configuration of a gas sensor element according to a third embodiment.

In comparison, in the present embodiment, as shown in FIG. 7, none of the four corner portions 22 (i.e., the pair of first corner portions 221 and the pair of second corner portions 222) is chamfered to have a chamfer surface. Therefore, at each of the corner portions 22, corresponding two of the plane portions 21 of the main body 2 intersect each other at 90°.

Moreover, in the present embodiment, the protective layer 4 has an average thickness of 400 μm at each of the plane portions 21 of the main body 2, an average thickness of 700 μm at each of the first corner portions 221 of the main body 2, and an average thickness of 620 μm at each of the second corner portions 222 of the main body 2.

Specifically, in the present embodiment, each of the four corner portions 22 of the main body 2 is defined to extend from the apex 220 of the corner portion 22 for a given distance (e.g., 0.4 mm) on each of the corresponding two plane portions 21 of the main body 2 which intersect each other at the apex 220 of the corner portion 22.

Figure 8:
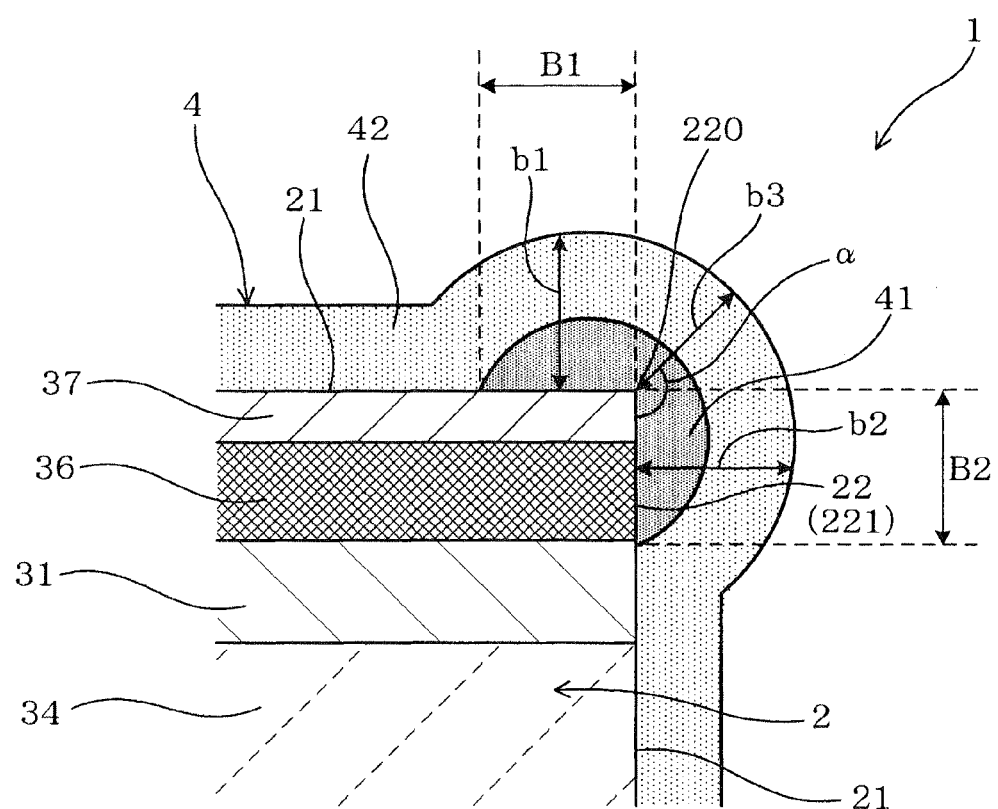
FIG. 8 is an enlarged view of an upper right corner portion of FIG. 7.

That is, as shown in FIG. 8, each of the four corner portions 22 of the main body 2 is defined to occupy first and second areas B1 and B2 respectively on the corresponding two plane portions 21 of the main body 2; the first and second areas B1 and B2 extend, respectively on the corresponding two plane portions 21, from the apex 220 of the corner portion 22 for the given distance.

Further, for each of the four corner portions 22 of the main body 2, the average thickness of the protective layer 4 at the corner portion 22 is determined by: (1) measuring values of the thickness of the protective layer 4 in the first area B1 in a direction perpendicular to the first area B1, in the second area B2 in a direction perpendicular to the second area B2 and at the apex 220 of the corner portion 22 in a predetermined direction; and (2) taking an average of all the measured values of the thickness of the protective layer 4.

More specifically, in the present embodiment, as shown in FIG. 8, for each of the four corner portions 22 of the main body 2, the average thickness of the protective layer 4 at the corner portion 22 is determined by: (1) measuring a value b1 of the thickness of the protective layer 4 at the center of the first area B1 in the direction perpendicular to the first area B1, a value b2 of the thickness at the center of the second area B2 in the direction perpendicular to the second area B2, and a value b3 of the thickness at the apex 220 of the corner portion 22 in the predetermined direction which makes the same angle α (i.e., 135°) with both the first and second areas B1 and B2; and (2) taking an average of all the measured values b1-b3 of the thickness of the protective layer 4.

On the other hand, for each of the plane portions 21 of the main body 2, the average thickness of the protective layer 4 at the plane portion 21 is determined by first measuring values of the thickness of the protective layer 4 in a direction perpendicular to the plane portion 21 at a plurality of points on the plane portion 21 and then taking an average of all the measured values of the thickness of the protective layer 4.

With the above configuration of the gas sensor element 1 according to the present embodiment, it is also possible to reliably prevent all of the four corner portions 22 of the main body 2 from being damaged by water included in the measurement gas while ensuring prompt activation of the solid electrolyte body 31.

Fourth Embodiment

This embodiment illustrates a gas sensor element 1 which has a similar configuration to the gas sensor element 1 according to the third embodiment; accordingly, only the differences therebetween will be described hereinafter.

In the third embodiment, the inner protective layer 41 is formed on the main body 2 of the gas sensor element 1 so as to cover all the four corner portions 22 (i.e., the pair of first corner portions 221 and the pair of second corner portions 222) of the main body 2 (see FIG. 7).

Figure 9:
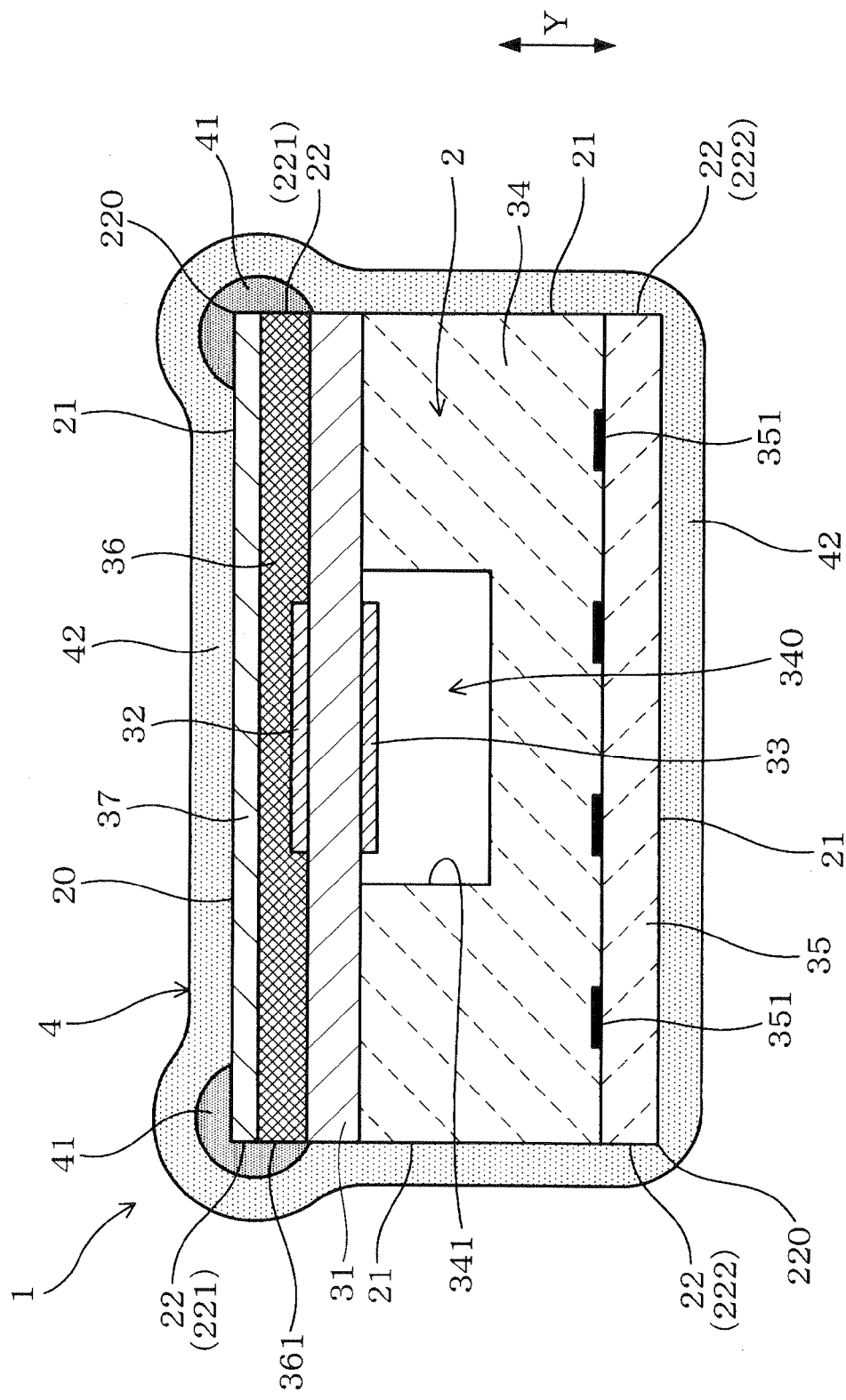
FIG. 9 is a cross-sectional view illustrating the overall configuration of a gas sensor element according to a fourth embodiment.

In comparison, in the present embodiment, as shown in FIG. 9, the inner protective layer 41 is formed on the main body 2 of the gas sensor element 1 so as to cover only the first corner portions 221 of the main body 2. That is, in the present embodiment, each of the second corner portions 222 of the main body 2 has no inner protective layer 41 formed thereon.

In addition, as in the third embodiment, none of the four corner portions 22 of the main body 2 is chamfered to have a chamfer surface. Therefore, at each of the corner portions 22, corresponding two of the plane portions 21 of the main body 2 intersect each other at 90°.

With the above configuration of the gas sensor element 1 according to the present embodiment, it is also possible to reliably prevent the first corner portions 221 of the main body 2 from being damaged by water included in the measurement gas while ensuring prompt activation of the solid electrolyte body 31.

Experiment

This experiment has been conducted to investigate the performance of the gas sensor element 1 according to the first embodiment.

In the experiment, gas sensor element samples E1-E36 and C1-C33 were tested.

Each of the samples E1-E36 had the same configuration as the gas sensor element 1 according to the first embodiment (see FIG. 1). That is, each of the samples E1-E36 included a protective layer which was comprised of an inner protective layer that covered only the four corner portions 22 of the main body 2 of the sample and an outer protective layer that covered the entire outer periphery of the main body 2 and the inner protective layer. However, as shown in FIG. 10A, both the average thickness of the protective layer at the first corner portions 221 of the main body 2 (referred to as "THICKNESS" in FIG. 10A for short) and the weight of the protective layer (referred to as "WEIGHT" in FIG. 10A for short) were varied for the samples E1-E36.

On the other hand, each of the samples C1-C33 had a different configuration from the gas sensor element 1 according to the first embodiment. More specifically, each of the samples C1-C33 included a protective layer which was comprised of an inner protective layer that covered the entire outer surface 20 of the main body 2 of the sample and an outer protective layer that covered the entire outer surface of the inner protective layer. Further, as shown in FIG. 10B, both the average thickness of the protective layer at the first corner portions 221 of the main body 2 (referred to as "THICKNESS" in FIG. 10B for short) and the weight of the protective layer (referred to as "WEIGHT" in FIG. 10B for short) were varied for the samples C1-C33.

First, each of the samples E1-E36 and C1-C33 was evaluated in terms of capability of preventing occurrence of cracks due to water.

More specifically, in the experiment, the sample was fixed with one of the chamfer surfaces 231 of the first corner portions 221 of the main body 2 of the sample extending parallel to the horizontal direction. Then, electric power was supplied to the heating element 351 of the heater layer 35 of the sample, thereby increasing the surface temperature of the sample to 750°. Thereafter, a given amount (e.g., 0.3 μL) of water was dropped on that part of the protective layer of the sample which covered the horizontally-extending chamfer surface 231 of the first corner portion 221 of the main body 2. Next, the sample was left unattended for 15 seconds, and then the surface temperature of the sample was again increased by supplying electric power to the heating element 351. After repeating the above processes for a predetermined number of times, it was checked whether cracks had occurred in the sample due to the water dropped on the sample.

Further, when cracks had not occurred, the sample was evaluated as being "good" and denoted by "○" in FIGS. 10A-10B. On the other hand, when cracks had occurred, the sample was evaluated as being "bad" and denoted by "x" in FIGS. 10A-10B.

In addition, when cracks had occurred in the sample, the amount of the measurement gas introduced to the measurement electrode 32 of the sample would be increased, thereby changing the sensing characteristics of the sample. Therefore, in the experiment, the checking of whether cracks had occurred in the sample was made by checking whether the sensing characteristics of the sample had been changed.

Secondly, each of the samples E1-E36 and C1-C33 was evaluated in terms of the activation time of the solid electrolyte body 31.

More specifically, the solid electrolyte body 31 generally has such a property that its resistance decreases with increase in its temperature. Therefore, in the experiment, the activation time of the solid electrolyte body 31 was measured as the time period from the start of the supply of electric power to the heating element 351 of the heater layer 35 of the sample until the resistance of the solid electrolyte body 31 had decreased to reach a predetermined value.

Further, when the measured activation time of the solid electrolyte body 31 was shorter than or equal to a predetermined amount of time, the sample was evaluated as being "good" and denoted by "○" in FIGS. 10A-10B. On the other hand, when the measured activation time was longer than the predetermined amount of time, the sample was evaluated as being "bad" and denoted by "x" in FIGS. 10A-10B.

As shown in FIG. 10B, among the samples C1-C33 which had the different configuration from the gas sensor element 1 according to the first embodiment, the samples C1-C3 were evaluated as being bad in terms of capability of preventing occurrence of cracks due to water. It should be noted that for each of the samples C1-C3, the average thickness of the protective layer at the first corner portions 221 of the main body 2 of the sample was less than 50 μm.

Moreover, the samples C11, C14, C17, C19, C21, C23, C26, C29, C31 and C33 were evaluated as being bad in terms of the activation time of the solid electrolyte body 31. It should be noted that for each of the samples C11, C14, C17, C19, C21, C23, C26, C29, C31 and C33, the weight of the protective layer of the sample was greater than or equal to 68 mg.

In comparison, as shown in FIG. 10A, among the samples E1-E36 which had the same configuration as the gas sensor element 1 according to the first embodiment, the samples E1 and E2 were evaluated as being bad in terms of capability of preventing occurrence of cracks due to water. It should be noted that for each of the samples E1 and E2, the average thickness of the protective layer at the first corner portions 221 of the main body 2 of the sample was less than 50 μm.

Moreover, the samples E34 and E36 were evaluated as being bad in terms of the activation time of the solid electrolyte body 31. It should be noted that for each of the samples E34 and E36, the weight of the protective layer of the sample was greater than or equal to 68 mg.

In addition, all the other samples E3-E33 and E35 were evaluated as being good in terms of both capability of preventing occurrence of cracks due to water and the activation time of the solid electrolyte body 31.

Figure 10C:
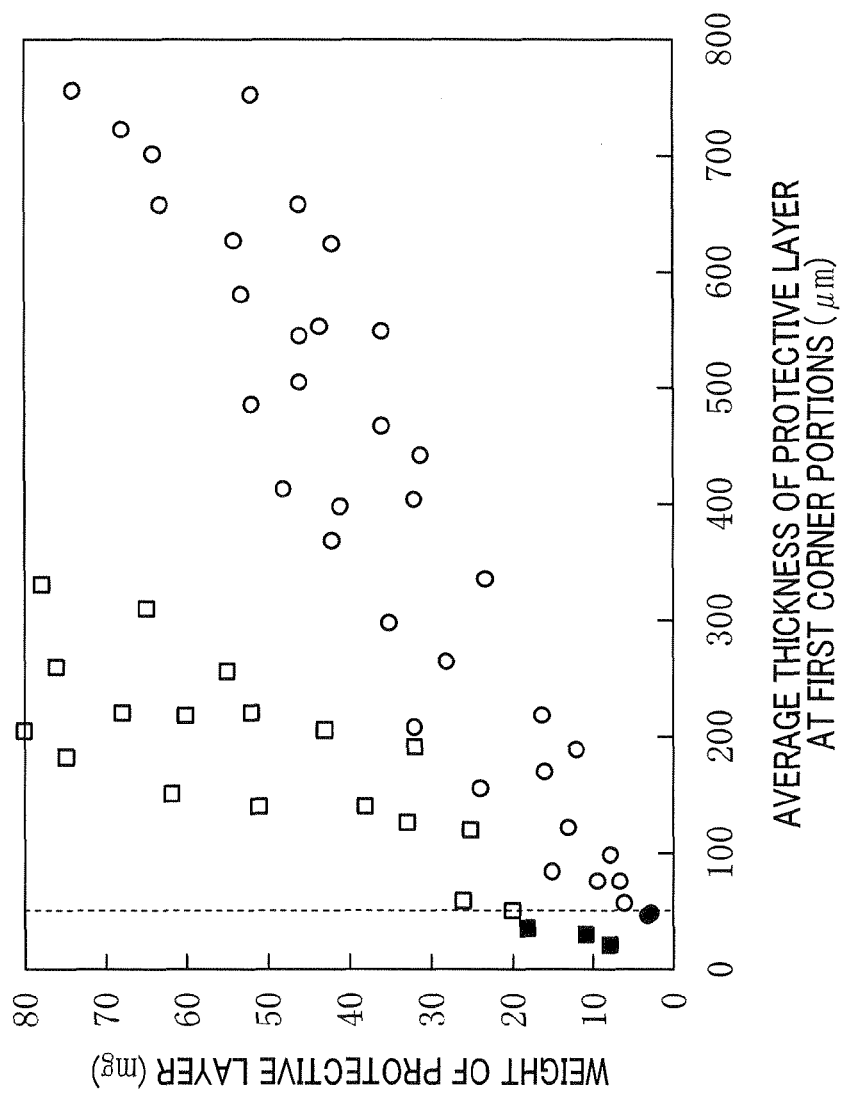
FIG. 10C is a graphical representation showing the evaluation results of all the samples E1-E36 and C1-C33.

The evaluation results of the samples E1-E36 and C1-C33 are also graphically shown in FIG. 10C.

In FIG. 10C, the vertical axis represents the weight of the protective layer, and the horizontal axis represents the average thickness of the protective layer at the first corner portions 221 of the main body 2. Moreover, the plots of "○" represent those of the samples E1-E36 which were evaluated as being good in terms of capability of preventing occurrence of cracks due to water; the plots of "●" represent those of the samples E1-E36 which were evaluated as being bad in terms of capability of preventing occurrence of cracks due to water; the plots of "□" represent those of the samples C1-C33 which were evaluated as being good in terms of capability of preventing occurrence of cracks due to water; the plots of "■" represent those of the samples C1-C33 which were evaluated as being bad in terms of capability of preventing occurrence of cracks due to water.

As can be seen from FIG. 10C, for the samples C1-C33 which had the different configuration from the gas sensor element 1 according to the first embodiment, the weight of the protective layer rapidly increased with the average thickness of the protective layer at the first corner portions 221 of the main body 2. In comparison, for the samples E1-E36 which had the same configuration as the gas sensor element 1 according to the first embodiment, the weight of the protective layer gradually increased with the average thickness of the protective layer at the first corner portions 221 of the main body 2.

Accordingly, from the above evaluation results, it is made clear that with the configuration of the gas sensor element 1 according to the first embodiment, it is possible to increase the average thickness of the protective layer at the first corner portions 221 of the main body 2 while suppressing increase in the weight of the protective layer. Moreover, it is also made clear that for reliably preventing occurrence of cracks due to water, it is necessary to set the average thickness of the protective layer at the first corner portions 221 of the main body 2 to be greater than or equal to 50 μm.

Fifth Embodiment

This embodiment illustrates gas sensor elements 1 the configurations of which are similar to those of the gas sensor elements 1 according to the previous embodiments; accordingly, only the differences therebetween will be described hereinafter.

In the gas sensor elements 1 according to the first and third embodiments, the inner protective layer 41 is formed on the main body 2 so as to cover only the four corner portions 22 (i.e., the pair of first corner portions 221 and the pair of second corner portions 222) of the main body 2 (see FIGS. 1 and 7). Moreover, in the gas sensor elements 1 according to the second and fourth embodiments, the inner protective layer 41 is formed on the main body 2 so as to cover only the first corner portions 221 of the main body 2 (see FIGS. 6 and 9). That is, in the gas sensor elements 1 according to the first to the fourth embodiments, each of the four plane portions 21 of the main body 2 has no inner protective layer 41 formed thereon.

In comparison, as shown in FIGS. 11A-18C, in the gas sensor elements 1 according to the present embodiment, the inner protective layer 41 is formed on the main body 2 so as to cover the entire outer surface 20 of the main body 2. In other words, the inner protective layer 41 is formed so as to cover all the four plane portions 21 of the main body 2 as well as all the four corner portions 22 of the main body 2. Further, the outer protective layer 42 is formed on the inner protective layer 41 so as to cover the entire outer surface of the inner protective layer 41. In other words, the outer protective layer 42 is formed to cover the entire outer periphery of the main body 2 and the inner protective layer 41.

Further, in the first, third, fifth, and seventh gas sensor elements 1 according to the present embodiment, which are respectively shown in FIGS. 11A-11C, FIGS. 13A-13C, FIGS. 15A-15C and FIGS. 17A-17C, the average thickness of the inner protective layer 41 at the four corner portions 22 (i.e., the pair of first corner portions 221 and the pair of second corner portions 222) of the main body 2 is larger than that at the four plane portions 21 of the main body 2. Moreover, the average thickness of the outer protective layer 42 is constant over the entire outer surface of the inner protective layer 41.

Consequently, the average thickness of the protective layer 4 at the four corner portions 22 of the main body 2 is also larger than that at the four plane portions 22 of the main body 2.

In the second, fourth, sixth and eighth gas sensor elements 1 according to the present embodiment, which are respectively shown in FIGS. 12A-12C, FIGS. 14A-14C, FIGS. 16A-16C and FIGS. 18A-18C, the average thickness of the inner protective layer 41 at the first corner portions 221 of the main body 2 is larger than those at the second corner portions 222 and at the plane portions 21 of the main body 2. Moreover, the average thickness of the outer protective layer 42 is constant over the entire outer surface of the inner protective layer 41. Consequently, the average thickness of the protective layer 4 at the first corner portions 221 of the main body 2 is also larger than those at the second corner portions 222 and at the plane portions 21 of the main body 2.

In the first, second, fifth and sixth gas sensor elements 1 according to the present embodiment, each of the four corner portions 22 of the main body 2 is chamfered, as shown in FIGS. 11A-11C, FIGS. 12A-12C, FIGS. 15A-15C and FIGS. 16A-16C.

In the third, fourth, seventh and eighth gas sensor elements 1 according to the present embodiment, none of the four corner portions 22 of the main body 2 is chamfered, as shown in FIGS. 13A-13C, FIGS. 14A-14C, FIGS. 17A-17C and FIGS. 18A-18C.

Next, a method of forming the protective layer 4 in the first to the fourth gas sensor elements 1 according to the present embodiment will be described.

First, the main body 2 is dipped into a slurry material 410a for forming the inner protective layer 41, which has a viscosity in the range of 100 to 800 mPa·s, and then raised out of the slurry material 410a. Consequently, the slurry material 410a is applied on the entire outer surface 20 of the main body 2, as shown in FIGS. 11A, 12A, 13A and 14A.

Secondly, a paste material 410b for forming the inner protective layer 41, which has a viscosity in the range of 1500 to 6000 mPa·s, is applied only on predetermined parts of the slurry material 410a applied on the main body 2.

Figure 11A:
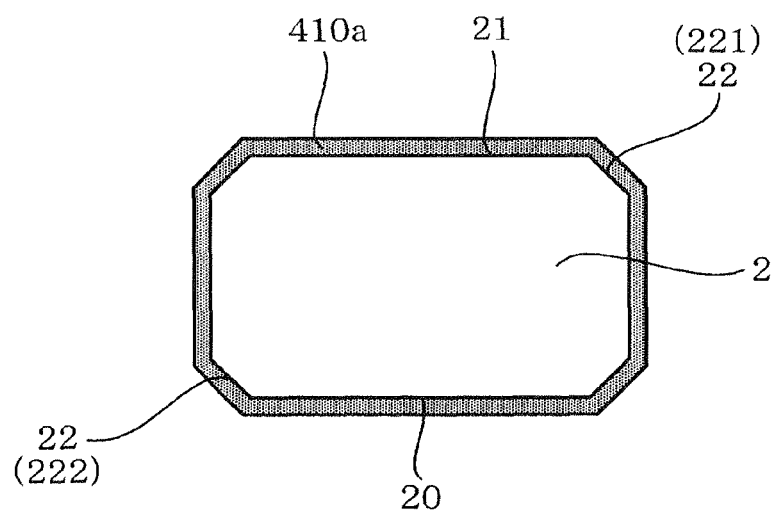
FIGS. 11A-11C are schematic views illustrating both a first gas sensor element according to a fifth embodiment and a method of manufacturing the first gas sensor element.
Figure 11B:
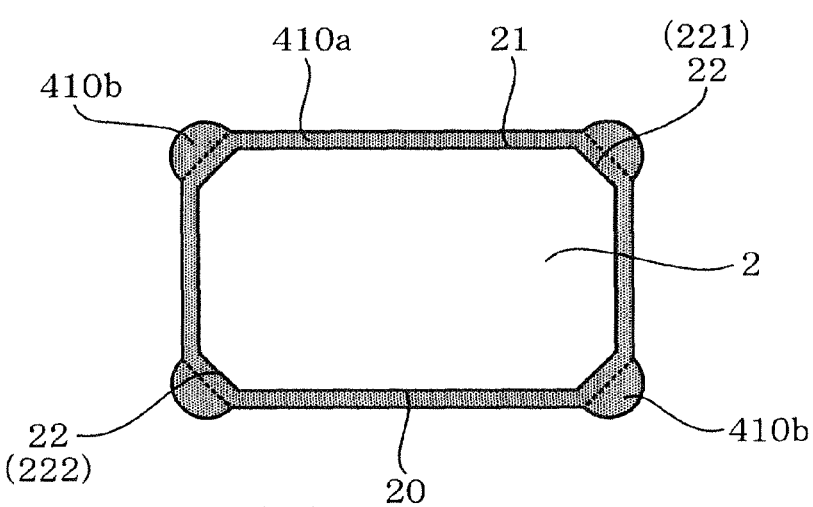
Figure 11C:
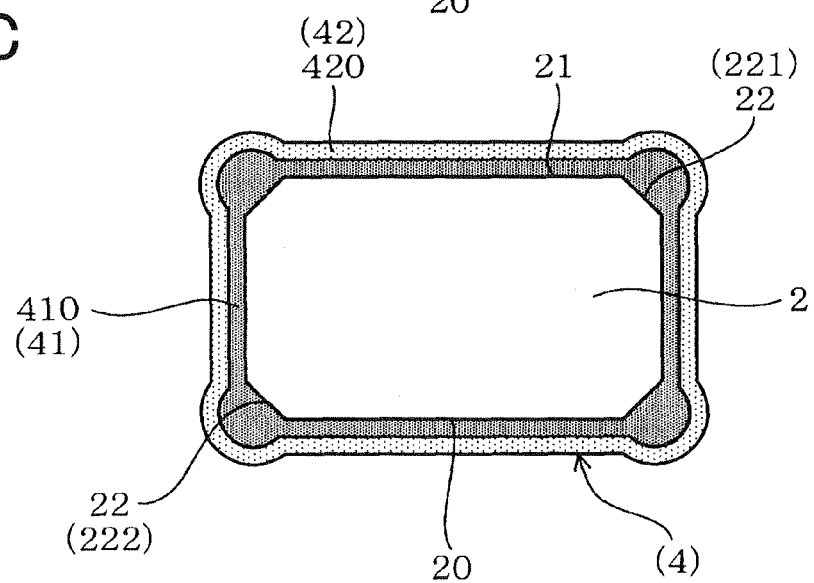
Figure 12A:
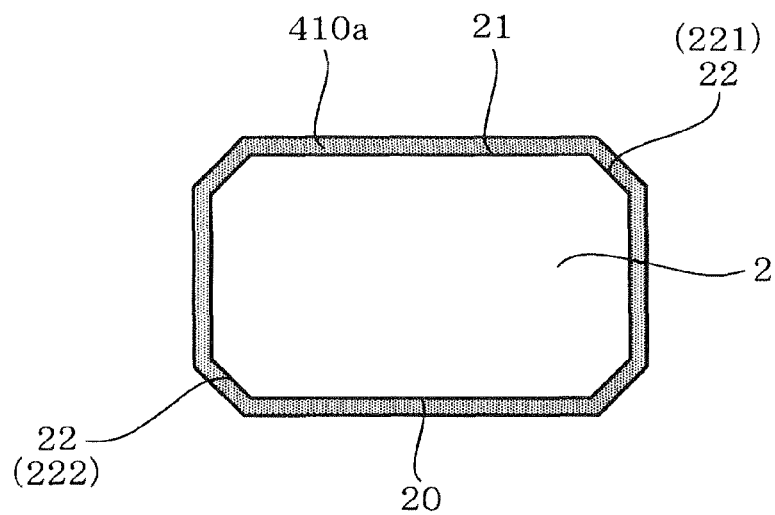
FIGS. 12A-12C are schematic views illustrating both a second gas sensor element according to the fifth embodiment and a method of manufacturing the second gas sensor element.
Figure 12B:
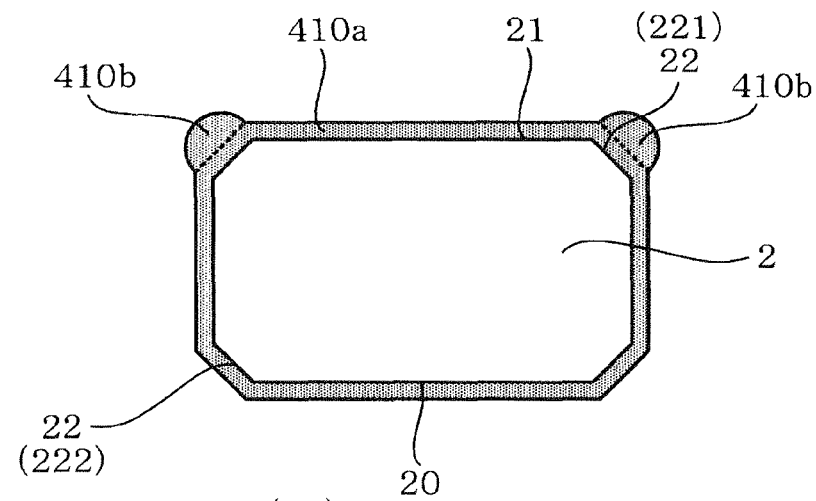
Figure 12C:
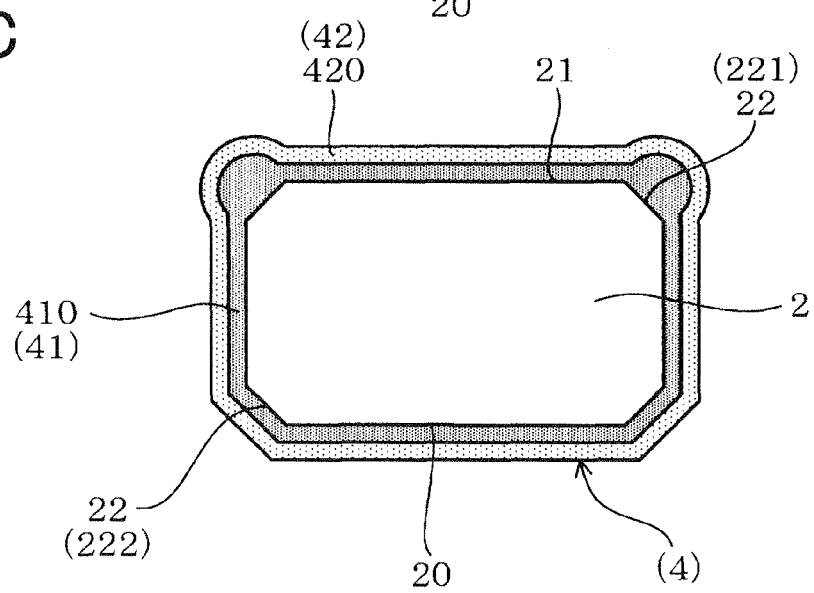
Figure 13A:
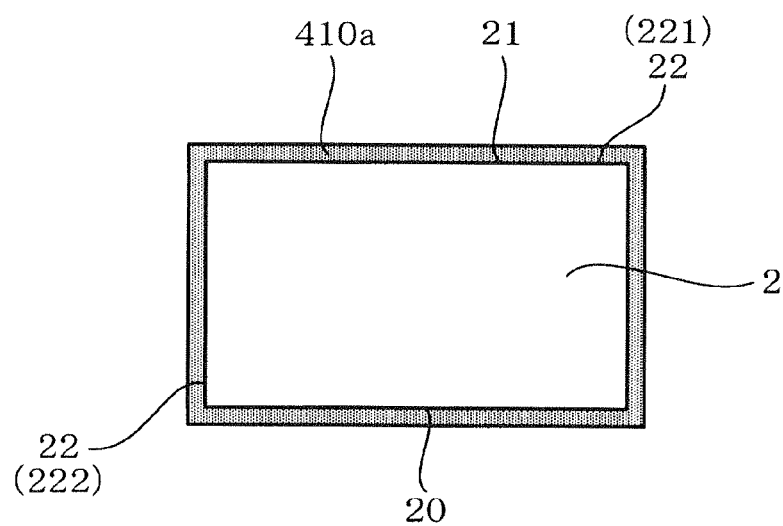
FIGS. 13A-13C are schematic views illustrating both a third gas sensor element according to the fifth embodiment and a method of manufacturing the third gas sensor element.
Figure 13B:
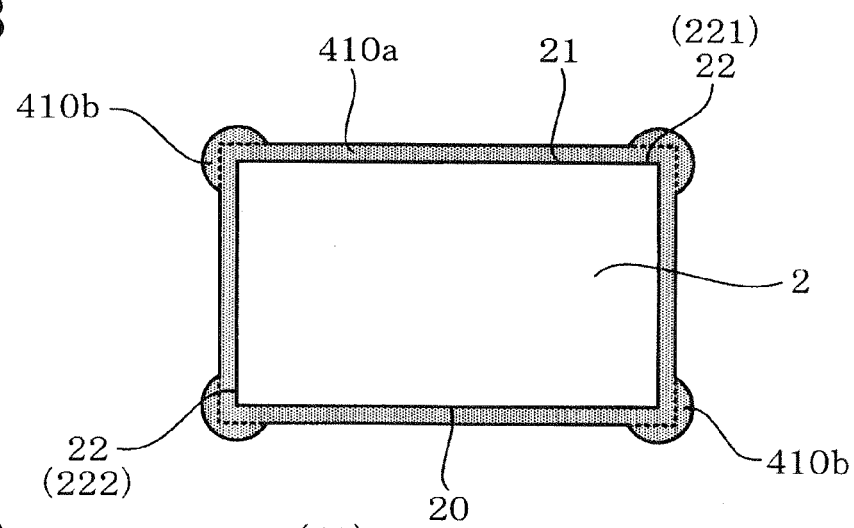
Figure 13C:
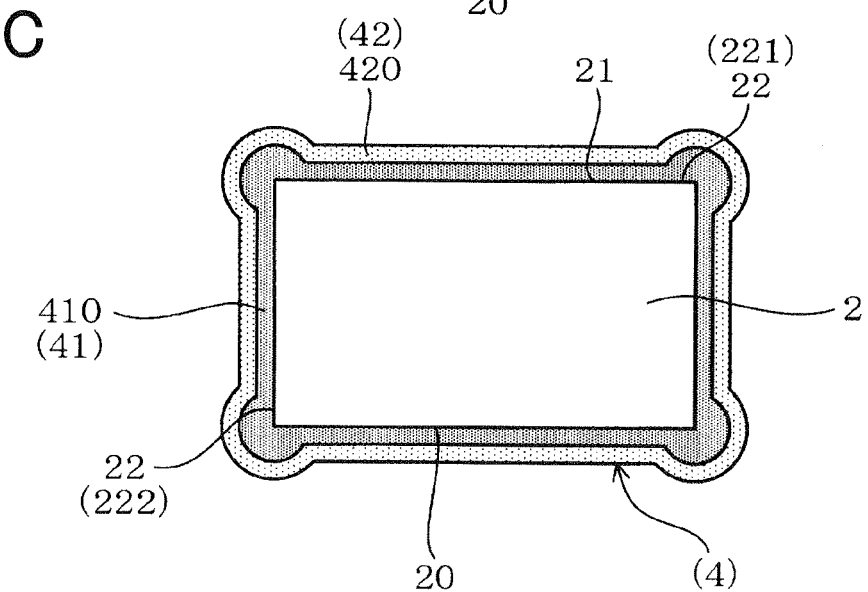
Figure 14A:
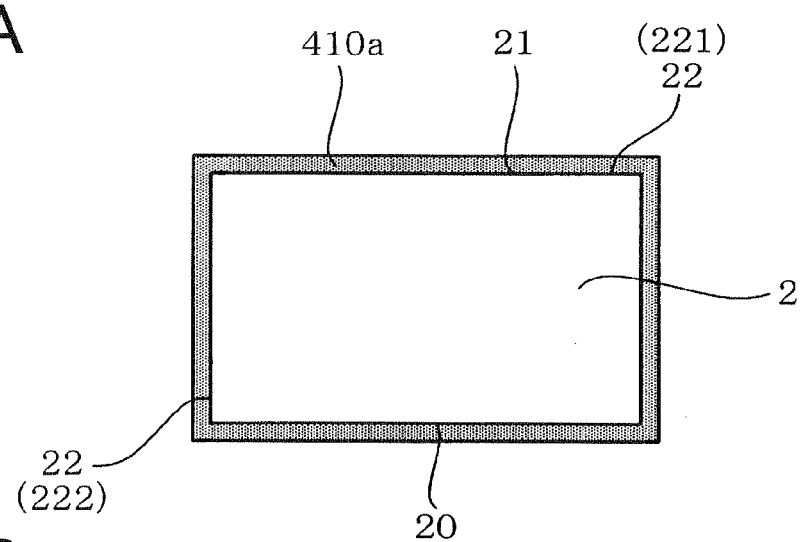
FIGS. 14A-14C are schematic views illustrating both a fourth gas sensor element according to the fifth embodiment and a method of manufacturing the fourth gas sensor element.
Figure 14B:
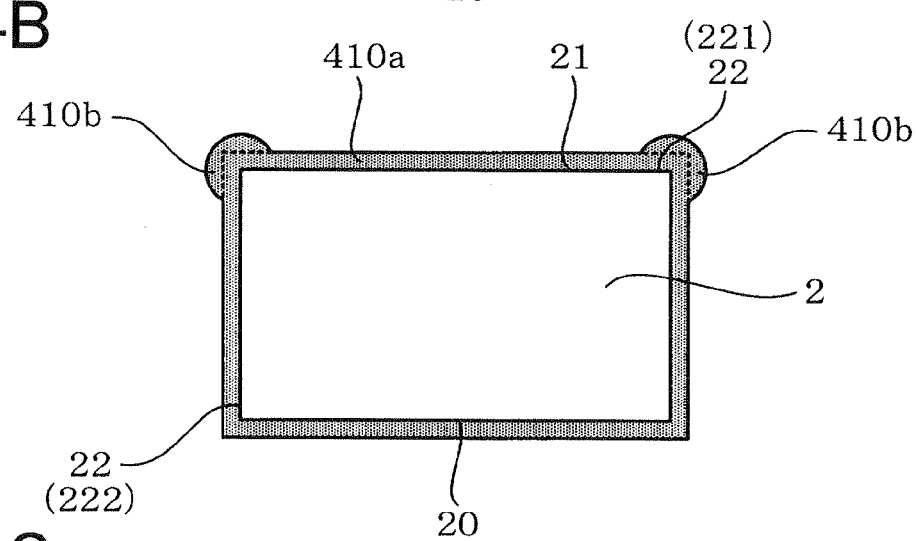
Figure 14C:
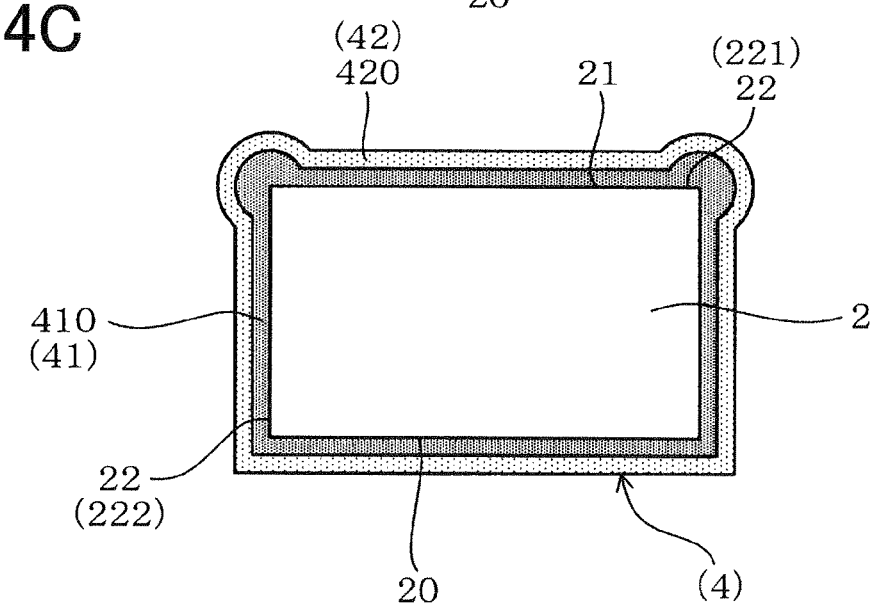

More specifically, in the first and third gas sensor elements 1 according to the present embodiment, the paste material 410b is applied only on those four parts of the slurry material 410a which respectively cover the four corner portions 22 of the main body 2, as shown in FIG. 11B and FIG. 13B. On the other hand, in the second and fourth gas sensor elements 1 according to the present embodiment, the paste material 410b is applied only on those two parts of the slurry material 410a which respectively cover the two first corner portions 221 of the main body 2, as shown in FIG. 12B and FIG. 14B.

Thirdly, the main body 2, which has the materials 410a and 410b for forming the inner protective layer 41 applied thereon, is dipped into a slurry material 420 for forming the outer protective layer 42, and then raised out of the slurry material 420. Consequently, the slurry material 420 is applied to cover the entire outer periphery of the materials 410a and 410b for forming the inner protective layer 41, as shown in FIGS. 11C, 12C, 13C and 14C. In addition, the slurry material 420 has a viscosity in the range of 100 to 1200 mPa·s.

Fourthly, the main body 2, which has the materials 410a, 410b and 420 applied thereon, is heated at 800 to 1000° C. for one to two hours. Consequently, all the materials 410a, 410b and 420 are dried and fired, thereby forming the inner and outer protective layers 41 and 42 on the main body 2.

As a result, the protective layer 4, which is comprised of the first and outer protective layers 41 and 42, is formed on the outer surface 20 of the main body 2.

Next, a method of forming the protective layer 4 in the fifth to the eighth gas sensor elements 1 according to the present embodiment will be described.

First, the paste material 410b for forming the inner protective layer 41 is applied only on predetermined portions of the main body 2. In addition, as described above, the viscosity of the paste material 410b is in the range of 1500 to 6000 mPa·s.

Figure 15A:
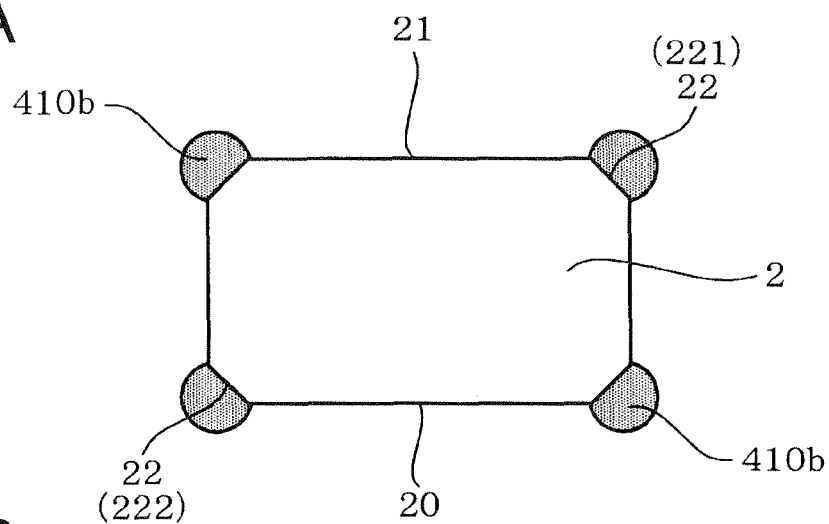
FIGS. 15A-15C are schematic views illustrating both a fifth gas sensor element according to the fifth embodiment and a method of manufacturing the fifth gas sensor element.
Figure 15B:
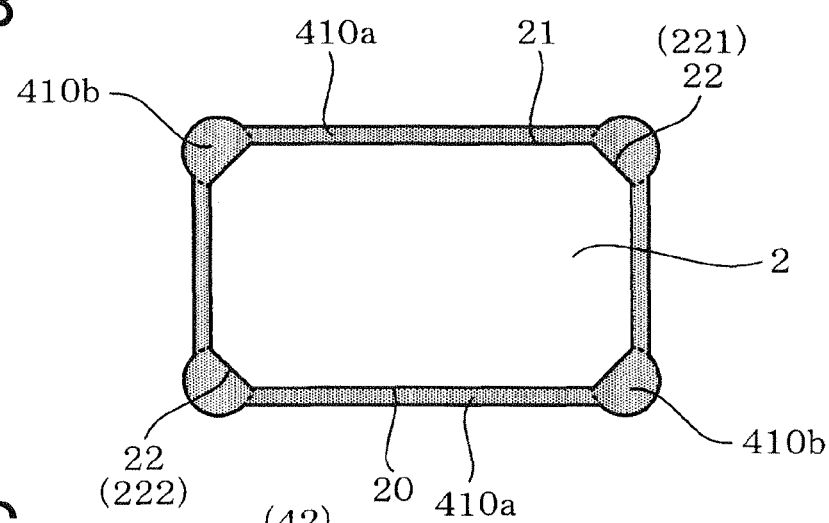
Figure 15C:
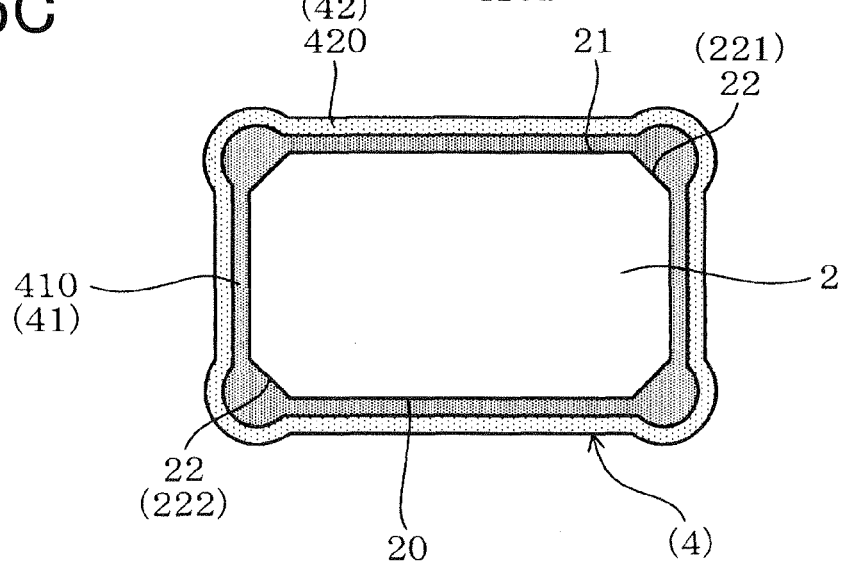
Figure 16A:
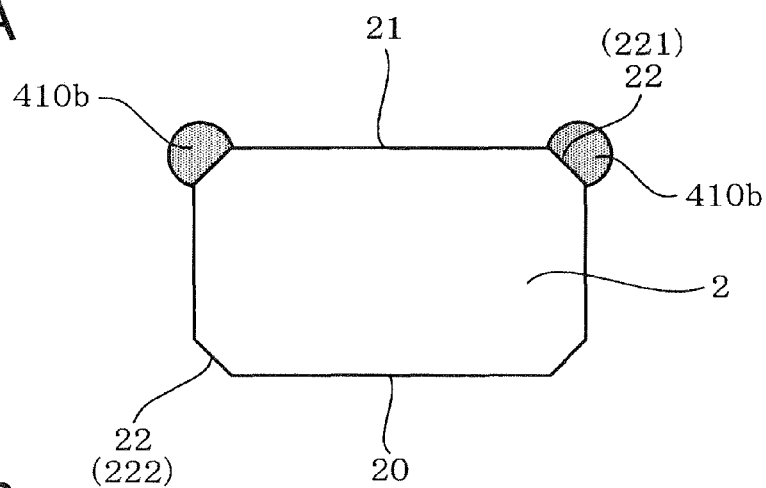
FIGS. 16A-16C are schematic views illustrating both a sixth gas sensor element according to the fifth embodiment and a method of manufacturing the sixth gas sensor element.
Figure 16B:
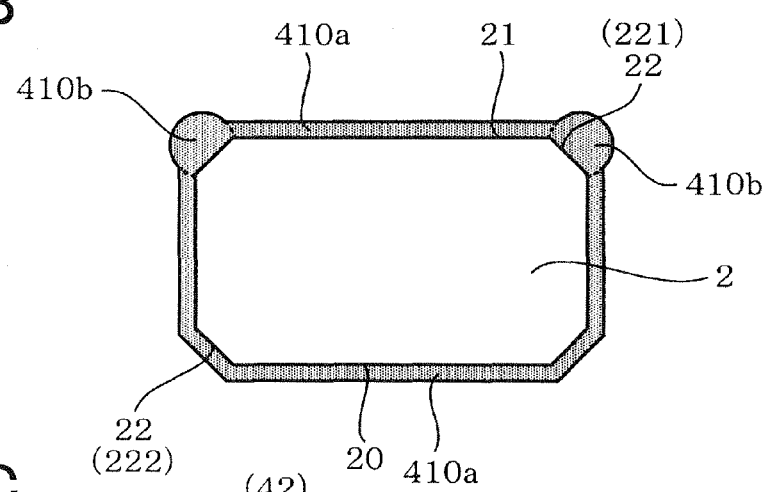
Figure 16C:
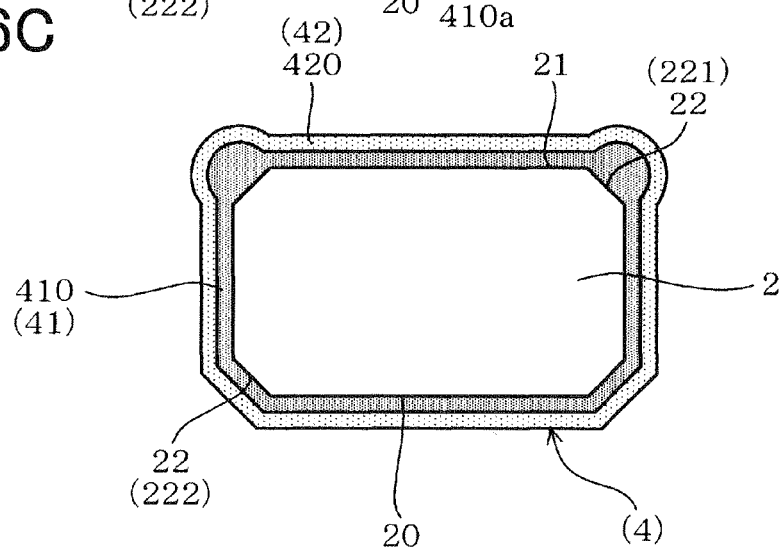
Figure 17A:
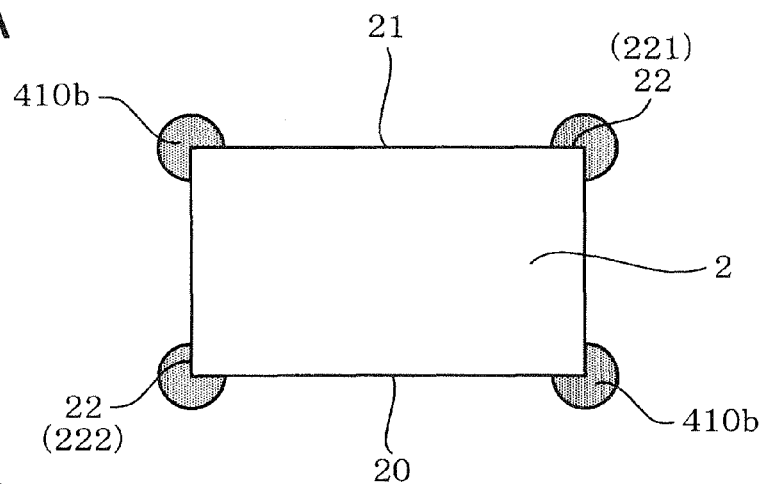
FIGS. 17A-17C are schematic views illustrating both a seventh gas sensor element according to the fifth embodiment and a method of manufacturing the seventh gas sensor element.
Figure 17B:
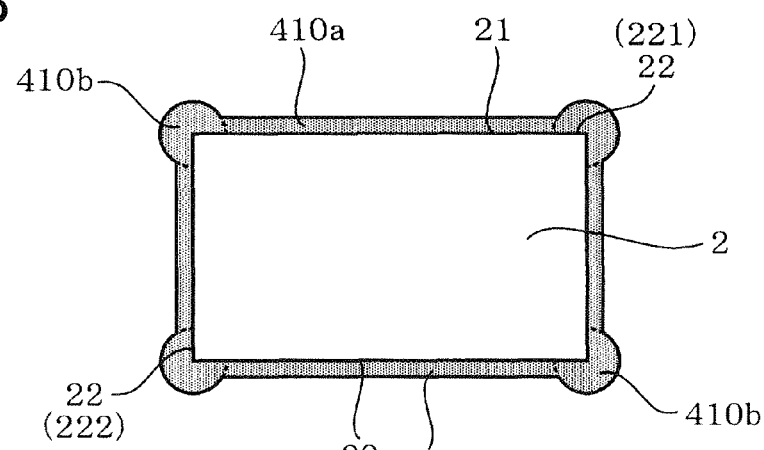
Figure 17C:
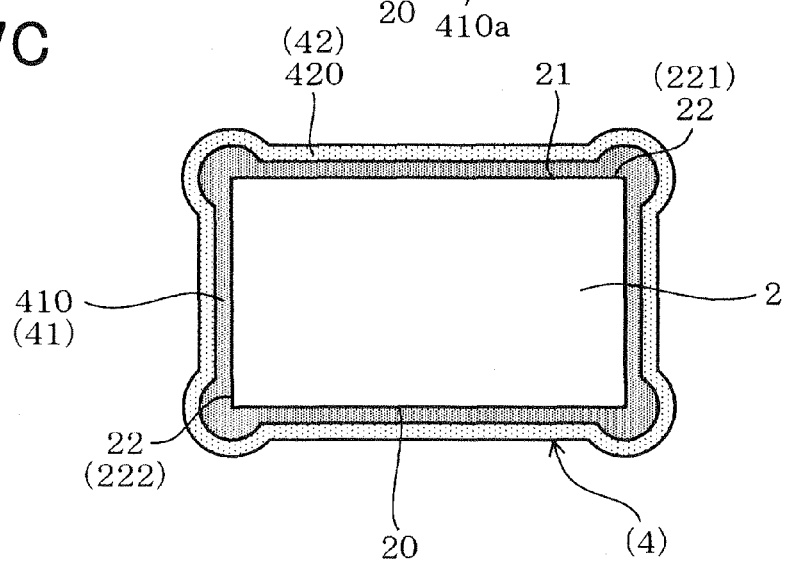
Figure 18A:
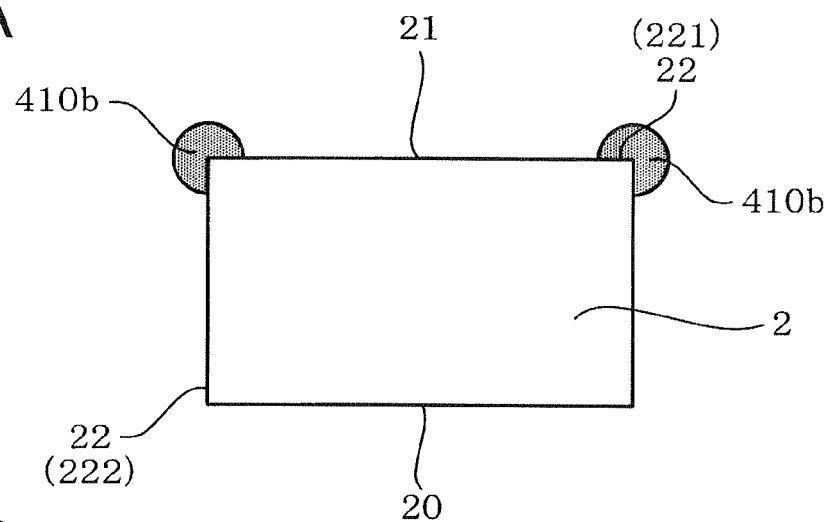
FIGS. 18A-18C are schematic views illustrating both an eighth gas sensor element according to the fifth embodiment and a method of manufacturing the eighth gas sensor element.
Figure 18B:
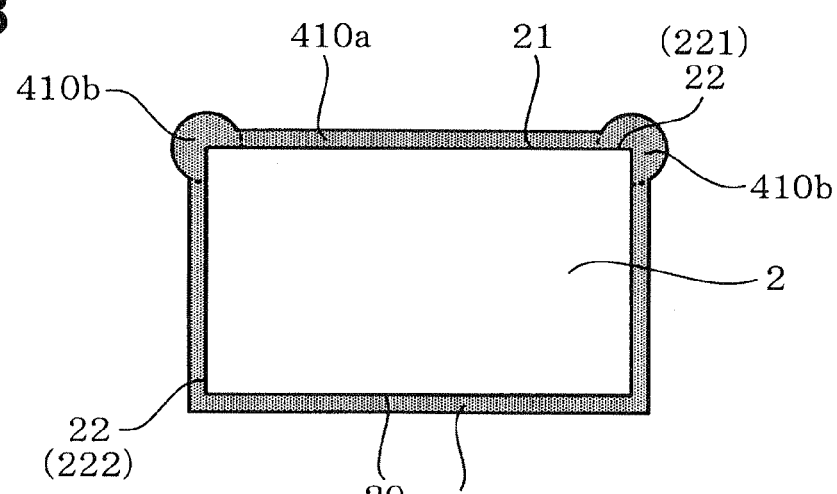
Figure 18C:
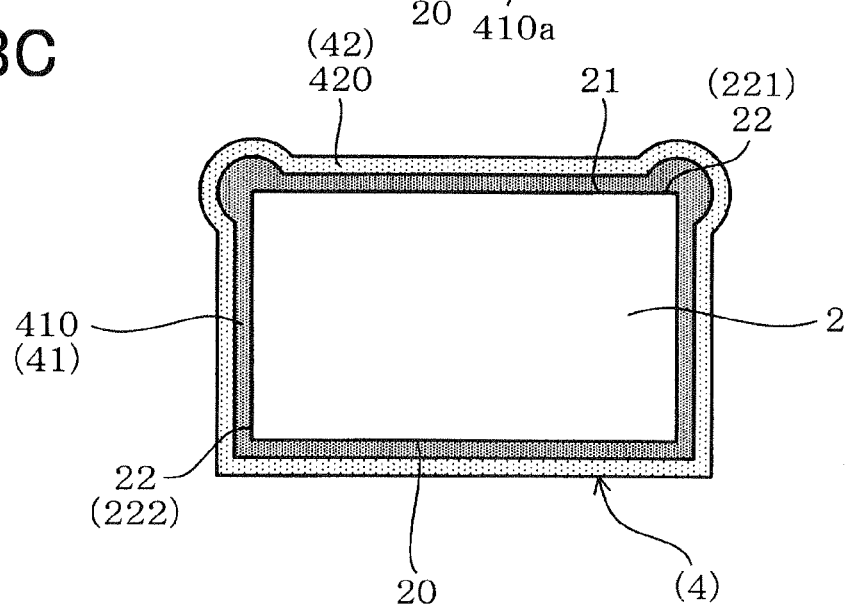

More specifically, in the fifth and seventh gas sensor elements 1 according to the present embodiment, the paste material 410b is applied only on the four corner portions 22 of the main body 2, as shown in FIG. 15A and FIG. 17A. On the other hand, in the sixth and eighth gas sensor elements 1 according to the present embodiment, the paste material 410b is applied only on the two first corner portions 221 of the main body 2, as shown in FIG. 16A and FIG. 18A.

Secondly, the main body 2, which has the paste material 410b applied thereon, is dipped into the slurry material 410a for forming the inner protective layer 41, and then raised out of the slurry material 410a. Consequently, the slurry material 410a is applied to cover the entire outer periphery of the main body 2 and the paste material 410b, as shown in FIGS. 15B, 16B, 17B and 18B. In addition, as described above, the viscosity of the slurry material 410a is in the range of 100 to 800 mPa·s.

Thirdly, the main body 2, which has the materials 410a and 410b for forming the inner protective layer 41 applied thereon, is dipped into the slurry material 420 for forming the outer protective layer 42, and then raised out of the slurry material 420. Consequently, the slurry material 420 is applied to cover the entire outer periphery of the materials 410a and 410b for forming the inner protective layer 41, as shown in FIGS. 15C, 16C, 17C and 18C. In addition, as described above, the viscosity of the slurry material 420 is in the range of 100 to 1200 mPa·s.

Fourthly, the main body 2, which has the materials 410a, 410b and 420 applied thereon, is heated at 800 to 1000° C. for one to two hours. Consequently, all the materials 410a, 410b and 420 are dried and fired, thereby forming the inner and outer protective layers 41 and 42 on the main body 2.

As a result, the protective layer 4, which is comprised of the inner and outer protective layers 41 and 42, is formed on the outer surface 20 of the main body 2.

As described above, in the first to the eighth gas sensor elements 1 according to the present embodiment, the inner protective layer 41 is formed so as to cover the entire outer surface 20 of the main body 2; the outer protective layer 42 is formed so as to cover the entire outer surface of the inner protective layer 41.

With the above formation of the inner and outer protective layers 41 and 42, it is possible to secure high joining strength between the outer surface 20 of the main body 2 and the outer protective layer 42.

While the above particular embodiments have been shown and described, it will be understood by those skilled in the art that various modifications, changes, and improvements may be made without departing from the spirit of the invention.

For example, in the first embodiment, the gas sensor element 1 is configured as an A/F ratio sensor element to sense the A/F ratio of air-fuel mixture supplied to an internal combustion engine of a motor vehicle.

However, the gas sensor element 1 may also be configured as an oxygen sensor element to sense the concentration of oxygen in the exhaust gas from an internal combustion engine of a motor vehicle. More specifically, in this case, the concentration of oxygen in the exhaust gas may be determined based on the electromotive force created between the measurement and reference electrodes 32 and 33; the electromotive force depends on the ratio between the concentration of oxygen in the measurement gas (i.e., the exhaust gas) and the concentration of oxygen in the reference gas (i.e., air).

In the first embodiment, the inner protective layer 41 is formed so as to cover the entire chamfer surfaces 231 of the first corner portions 221 and the entire chamfer surfaces 232 of the second corner portion 222 of the main body 2.

However, the inner protective layer 41 may also be formed so as to cover only central parts of the chamfer surfaces 231 and 232 of the first and second corner portions 221 and 222 of the main body 2.

In the first embodiment, in the first application step of the method of manufacturing the gas sensor element 1, the first material 410 is applied using the dispenser 61.

However, the first material 410 may also be applied by other means, for example using an injector or a spray.

Moreover, in the second application step of the method of manufacturing the gas sensor element 1, the second material 420 is applied by dipping.

However, the second material 420 may also be applied in other manners, for example using a spray.

In the first embodiment, each of the first corner portions 221 of the main body 2 is chamfered to have the chamfer surface 231; each of the second corner portions 222 of the main body 2 is also chamfered to have the chamfer surface 232.

However, each of the first and second corner portions 221 and 222 of the main body 2 may also be rounded, instead of being chamfered, to have a rounded surface. In this case, the measurement gas inlets 361 of the diffusion-resistant layer 36 may be respectively formed in the rounded surfaces of the first corner portions 221 of the main body 2.

What is claimed is:

1. A gas sensor element having a main body that comprises:
   a solid electrolyte body having oxygen ion conductivity;
   a measurement gas-side electrode and a reference gas-side electrode that are respectively provided on an opposite pair of first-side and second-side surfaces of the solid electrolyte body;
   a porous diffusion-resistant layer laminated on the first side of the solid electrolyte body so that a measurement gas passes through the diffusion-resistant layer to make contact with the measurement gas-side electrode; and
   a heater layer which is laminated on the second side of the solid electrolyte body and includes a heater that generates heat upon being supplied with electric power,
   wherein
   the main body is substantially quadrangular in shape to have, a pair of plane portions that are opposite to each other in a lamination direction of the main body, a pair of plane portions that are opposite to each other in a direction perpendicular to the lamination direction, and four corner portions formed between the four plane portions,
   the four corner portions include a pair of diffusion-side corner portions that are located on the first side of the solid electrolyte body and each have formed therein a measurement gas inlet of the diffusion-resistant layer via which the measurement gas is introduced to the diffusion-resistant layer,
   on the main body, there are provided a protective layer which is comprised of a first protective layer that covers, among the four corner portions, at least the pair of diffusion-side corner portions and a second protective layer that covers an entire outer periphery of the main body including the first protective layer, and
   the protective layer has a larger thickness at the diffusion-side corner portions than at the an average thickness for each of the plane portions of the main body.

2. The gas sensor element as set forth in claim 1, wherein the first protective layer is made of first ceramic particles and the second protective layer is made of second ceramic particles, and
   the first ceramic particles have a smaller average particle diameter than the second ceramic particles.

3. The gas sensor element as set forth in claim 2, wherein the average particle diameter of the first ceramic particles is in the range of 2 to 14 μm, and the average particle diameter of the second ceramic particles is in the range of 14 to 35 μm.

4. The gas sensor element as set forth in claim 1, wherein the first protective layer has a smaller porosity than the second protective layer.

5. The gas sensor element as set forth in claim 4, wherein the porosity of the first protective layer is in the range of 10 to 45%, and the porosity of the second protective layer is in the range of 45 to 70%.

6. The gas sensor element as set forth in claim 1, wherein the thickness of the protective layer at the diffusion-side corner portions of the main body is greater than or equal to 50 μm.

7. The gas sensor element as set forth in claim 1, wherein the four corner portions of the main body include, in addition to the pair of diffusion-side corner portions, a pair of heater-side corner portions that are laminated on the second side of the solid electrolyte body,
   the first protective layer covers the heater-side corner portions of the main body as well as the diffusion-side corner portions, and
   the protective layer has a larger thickness at the heater-side corner portions than at the an average thickness for each of the plane portions of the main body.

8. The gas sensor element as set forth in claim 7, wherein the thickness of the protective layer at the diffusion-side corner portions of the main body is larger than that at the heater-side corner portions of the main body.

9. The gas sensor element as set forth in claim 1, wherein each of the diffusion-side corner portions of the main body is chamfered to have a chamfer surface or rounded to have a rounded surface, and
   in the chamfer surface or the rounded surface, there is formed the measurement gas inlet of the diffusion-resistant layer.

10. The gas sensor element as set forth in claim 9, wherein each of the heater-side corner portions of the main body is also chamfered to have a chamfer surface or rounded to have a rounded surface.

11. A method of manufacturing the gas sensor element as set forth in claim 1, the method comprising the steps of:
    applying a first material, which is prepared for forming the first protective layer, on at least the diffusion-side corner portions of the main body;
    applying a second material, which is prepared for forming the second protective layer, to cover an entire outer periphery of the main body including the applied first material; and
    heat-treating both the applied first and second materials to respectively form the first and second protective layers.

12. The method as set forth in claim 11, wherein the first material is applied using a dispenser.

13. The method as set forth in claim 11, wherein the second material is applied by dipping.

14. The method as set forth in claim 11, wherein the first material has a higher viscosity than the second material.

15. The method as set forth in claim 14, wherein the viscosity of the first material is in the range of 1500 to 6000 mPa·s, and the viscosity of the second material is in the range of 100 to 1200 mPa·s.

16. A gas sensor characterized by comprising the gas sensor element as set forth in claim 1.

* * * * *